(12) United States Patent
Pratt et al.

(10) Patent No.: US 11,253,401 B2
(45) Date of Patent: Feb. 22, 2022

(54) WOUND THERAPY SYSTEM WITH WOUND VOLUME ESTIMATION

(71) Applicant: KCI LICENSING, INC., San Antonio, TX (US)

(72) Inventors: Benjamin A. Pratt, Poole (GB); Justin Rice, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 314 days.

(21) Appl. No.: 16/365,418

(22) Filed: Mar. 26, 2019

(65) Prior Publication Data

US 2020/0038249 A1 Feb. 6, 2020

Related U.S. Application Data

(60) Provisional application No. 62/714,229, filed on Aug. 3, 2018.

(51) Int. Cl.
*A61M 1/00* (2006.01)
*A61F 13/02* (2006.01)
(Continued)

(52) U.S. Cl.
CPC ....... *A61F 13/0216* (2013.01); *A61M 1/0023* (2013.01); *A61M 1/962* (2021.05);
(Continued)

(58) Field of Classification Search
CPC ........ A61F 13/0216; A61F 2013/00174; A61F 2013/8494; A61M 1/0023; A61M 35/006;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Philip R Wiest
*Assistant Examiner* — Gregory J Feulner

(57) ABSTRACT

A pump generates a vacuum at a wound site via first tubing. A negative pressure circuit is defined by a canister, the first tubing and the wound site. A controller of a therapy device operates the pump to apply a first negative pressure to the entirety of the negative pressure circuit, following which ambient air is allowed to flow into the negative pressure circuit. The controller also operates the pump to apply a second negative pressure to a selected portion of the negative pressure circuit exclusive of the wound site, following which ambient air is allowed to flow into the selected portion. A quantity of fluid to be delivered to the wound site via a second tubing is determined by comparing measured parameters related to the flow of air into the negative pressure circuit to parameters measured with respect to the flow of air into the selected portion.

12 Claims, 15 Drawing Sheets

(51) Int. Cl.
*A61B 5/00* (2006.01)
*A61F 13/00* (2006.01)
*A61F 13/84* (2006.01)
*A61F 13/40* (2006.01)

(52) U.S. Cl.
CPC ............ *A61M 1/964* (2021.05); *A61B 5/445* (2013.01); *A61F 2013/00174* (2013.01); *A61F 2013/8494* (2013.01); *A61M 35/006* (2013.01); *A61M 2205/3337* (2013.01); *A61M 2205/3344* (2013.01)

(58) Field of Classification Search
CPC ............ A61M 2205/3344; A61M 1/90; A61M 2039/242; A61M 1/742; A61M 2205/3331; A61M 2205/3334; A61M 3/022; A61M 3/0258; A61M 1/85; A61B 5/445; A61B 5/1073
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 10,188,776 B2 * | 1/2019 | Greener ............... A61M 1/74 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0030383 A1 * | 1/2009 | Larsen ............... A61M 1/74 604/290 |
| 2009/0227969 A1 | 9/2009 | Jaeb et al. |
| 2011/0213319 A1 | 9/2011 | Blott et al. |
| 2011/0224634 A1 | 9/2011 | Locke et al. |
| 2013/0211318 A1 * | 8/2013 | Croizat ............... A61M 1/0058 604/23 |
| 2015/0032031 A1 | 1/2015 | Hartwell |
| 2015/0231314 A1 * | 8/2015 | Robinson ......... A61F 13/00017 604/319 |
| 2015/0320603 A1 | 11/2015 | Locke et al. |
| 2016/0045648 A1 * | 2/2016 | Locke ............... F16M 11/046 604/318 |
| 2016/0166740 A1 * | 6/2016 | Hartwell ............... A61B 5/445 604/319 |
| 2016/0184497 A1 * | 6/2016 | Phillips ............... G16H 40/63 604/318 |
| 2017/0007752 A1 | 1/2017 | Freedman et al. |
| 2017/0209641 A1 | 7/2017 | Mercer et al. |
| 2018/0042521 A1 * | 2/2018 | Ryu ............... A61B 5/1073 |
| 2019/0295718 A1 * | 9/2019 | Lawhorn ............... G16H 20/40 |
| 2019/0365961 A1 * | 12/2019 | Walti ............... A61M 1/777 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |

(56) References Cited

FOREIGN PATENT DOCUMENTS

| | | |
|---|---|---|
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3 269 404 A1 | 1/2018 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2012/106590 A2 | 8/2012 |
| WO | WO-2013/066694 A2 | 5/2013 |
| WO | WO-2013/175309 A1 | 11/2013 |
| WO | WO-2015/008054 A1 | 1/2015 |
| WO | WO-2015/110409 A1 | 7/2015 |
| WO | WO-2015/110410 A1 | 7/2015 |
| WO | WO-2016/176513 A1 | 11/2016 |
| WO | WO-2018/013242 A1 | 1/2018 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion in International Application No. PCT/US2019/024117, dated Jun. 27, 2019.

* cited by examiner

WOUND THERAPY SYSTEM WITH WOUND VOLUME ESTIMATION

CROSS-REFERENCE TO RELATED APPLICATIONS

This application claims the benefit of priority to U.S. Provisional Application No. 62/714,229, filed on Aug. 3, 2018, which is incorporated herein by reference in its entirety.

BACKGROUND

The present disclosure relates generally to a wound therapy system, and more particularly to a wound therapy system configured to estimate a volume relative to a wound site.

Negative pressure wound therapy (NPWT) is a type of wound therapy that involves applying a negative pressure to a wound site to promote wound healing. Recent advancements in wound healing with NPWT involve applying topical fluids to wounds to work in combination with NPWT. However, it can be difficult to determine the appropriate volume of instillation fluid to deliver to the wound. Additionally, it can be difficult to accurately monitor and track healing progression of the wound over time. Accordingly, it would be advantageous to provide a system and method that would allow for accurate and reliable estimation of available space at a wound site into which instillation fluid could be delivered and estimation of the healing progression of the wound site over time. Advantageously, such a system and method would additionally allow for such volume determinations to be performed automatically by a controller, could be performed at any stage during the NPWT treatment, and could account for changes in the type or size of removed fluid canister used over the course of the NPWT treatment.

SUMMARY

In one implementation of the present disclosure, a wound therapy system includes a therapy device, tubing, a valve, and an opening formed through the first tubing portion. The therapy device includes a canister configured to collect wound exudate from a wound and a pump fluidly coupled to the canister and configured to draw a negative pressure within the canister. The tubing has a first end and a second end. The first end of the tubing is attached to and fluidly coupled to the canister. The valve is coupled to the tubing at a position located between the first end and the second end of the tubing. The valve is configured to prevent flow if a threshold minimum negative pressure is not met and to permit flow if the threshold negative pressure is met. A first tubing portion is defined between the first end of the tubing and the valve. A second tubing portion is defined between the second end of the tubing and the valve. The opening configured to allow for fluid communication between the first tubing portion and an ambient pressure atmosphere.

According to some embodiments, the tubing is defined by an outer wall. The opening extends through the outer wall of the tubing. According to some embodiments, the second end of the tubing is attached to a wound dressing configured to be sealed to a surface to define a treatment space. The fluid canister is in fluid communication with the treatment space when the valve is subject to a pressure that is less than or equal to the threshold minimum negative pressure.

According to some embodiments, the wound therapy system may further include a controller configured to operate the pump to draw a predetermined first negative pressure in the canister. The first predetermined negative pressure may be greater than the threshold minimum negative pressure. The controller may be configured to calculate a first volume based on a measured time required for pressure within the canister to increase from the predetermined first negative pressure to a predetermined baseline pressure.

According to some embodiments, the controller may further be configured to operate the pump to draw a predetermined second negative pressure within the canister and the treatment space that is less than the threshold minimum negative pressure. The controller further being configured to calculate a second volume based on a measured time required for pressure within the canister and the treatment space to increase from the predetermined second negative pressure to the predetermined baseline pressure.

According to some embodiments, the controller may further be configured to calculate the volume of the treatment space based on the difference between the first calculated volume and the second calculated volume. The controller may further be configured to calculate a volume of the treatment space based on subtracting a known volume of the tubing from a calculated difference between the first calculated volume and the second calculated volume.

According to some embodiments, a calibrated leak detector is fluidly connected to the opening of the tubing and is configured to measure the rate of air flowing through the opening. The calculations of the first volume and the second volume by the controller are each based on the rate of air flow through the opening detected by the leak detector.

According to some embodiments, the valve is configured to remain in an open configuration in which the first tubing section and the second tubing section are in fluid communication following the valve being subject to the threshold minimum negative pressure. The valve is resettable from the open configuration to the initial closed valve configuration in which fluid communication between the first tubing section and the second tubing section is prevented by the valve until a pressure less than or equal to the threshold negative pressure is met.

According to some embodiments, the wound therapy system further includes a first pressure sensor in fluid communication with the first tubing section. Following a predetermined time interval after detection of the predetermined first negative pressure within the first tubing section by the first pressure sensor, the controller may stop operation of the pump. The wound therapy system may further include a second pressure sensor in fluid communication with the second tubing section.

According to some embodiments, following a predetermined time interval after detection of the predetermined second negative pressure within the second tubing section by the second pressure sensor, the controller is configured to stop operation of the pump. The opening in the tubing may define a calibrated leak having a known dimension through which air from the ambient pressure atmosphere may flow into the tubing.

In one implementation of the present disclosure, a method of operating a wound therapy device includes operably connecting a first end of a fluid tube to a fluid canister and a pump of a therapy device and a second end of the fluid tube to a wound dressing. The pump is operated to apply a first predetermined negative pressure to a first volume including the fluid canister and excluding the wound dressing. The pump is stopped for a period of time during which the first predetermined negative pressure within the first volume increases to a baseline pressure over a first time period. A first capacity of the first volume is determined using the first time period. The pump is operated to apply a second predetermined negative pressure to a second volume which includes the first volume and the wound dressing. The pump is stopped for a period of time during which the second predetermined negative pressure within the second volume increases to the baseline pressure over a second time period. A second capacity of the second volume is determined using the second time period. A first quantity of wound dressing instillation fluid to be delivered is determined based at least in part upon a difference between the first capacity and the second capacity.

According to some embodiments, the first predetermined negative pressure is different than the second predetermined negative pressure. The first predetermined negative pressure may be greater than the second predetermined negative pressure.

According to some embodiments, a valve is operably connected to the fluid tube at a location between the first end and the second end of the fluid tube. The valve may be configured to prevent flow between the fluid tube and the wound dressing when the valve is subject to a pressure that is equal to or greater than the first predetermined negative pressure. According to some embodiments, the valve is configured to permit flow between the first portion of the interior of the fluid tubing and the wound dressing when the valve is subject to the second predetermined negative pressure.

According to some embodiments, the pump is operated to deliver the first quantity of wound dressing instillation fluid to the wound dressing. The pump is operated to apply the second predetermined negative pressure to the second volume at a point in time prior to the operation of the pump to apply the first predetermined negative pressure to the first volume.

According to some embodiments, after the step of delivering instillation fluid to the treatment space the pump is operated to apply a third predetermined negative pressure to the first volume. The pump is stopped for a period of time during which the third predetermined negative pressure within the first volume increases to a second baseline pressure over a third time period. After the pressure within the tubing has reached the second baseline pressure, the pump is operated to apply a fourth predetermined negative pressure to the second volume. The pump is stopped for a period of time during which the fourth predetermined negative pressure within the second volume increases to the second baseline pressure over a fourth time period.

According to some embodiments, the third predetermined negative pressure is greater than the fourth predetermined negative pressure. The third predetermined negative pressure is equal to the first predetermined negative pressure. According to some embodiments, the fourth predetermined negative pressure is equal to the second predetermined negative pressure.

According to some embodiments, the pump is operated to deliver a second wound dressing instillation fluid quantity to the wound dressing. The pump is operated to apply the fourth predetermined negative pressure to the second volume at a point in time prior to the operation of the pump to apply the third predetermined negative pressure to the first volume. The second quantity of wound dressing instillation fluid that is delivered to the wound dressing is based on a comparison of the third time period to the fourth time period. The relative difference between the first time period and the second time period may be greater than the relative difference between the third time period and the fourth time period. According to some embodiments, the first quantity of wound dressing instillation fluid is greater than the second quantity of wound dressing instillation fluid.

According to some embodiments, the fluid canister is empty when the pump is operated apply the first predetermined negative pressure and when the pump is operated to apply the second predetermined negative pressure, and the fluid canister is at least partially full when the pump is operated apply the third predetermined negative pressure and when the pump is operated to apply the fourth predetermined negative pressure.

According to some embodiments, the relative difference between the first time period and the second time period is less than the relative difference between the third time period and the fourth time period. The first quantity of wound dressing instillation fluid is less than the second quantity of wound dressing instillation fluid.

In one implementation of the present disclosure, a method of delivering an instillation fluid to a wound dressing includes measuring a first volume representative of at least a fluid canister associated with a wound therapy device and measuring a second volume representative of at least the fluid canister and a wound dressing. The first volume is subtracted from the second volume to obtain a third volume. An instillation volume is calculated based on the third volume. A quantity of instillation fluid equal to the instillation volume is delivered, via the wound therapy device to the wound dressing.

According to some embodiments, calculating the instillation volume includes multiplying the third volume by an instillation adjustment factor, and the first volume excludes the volume of wound dressing.

According to some embodiments, the first volume is measured by operating a pump fluidly attached to the fluid canister to entirely fill the first volume with a first quantity of fluid and measuring a volume of the first quantity of fluid. The fluid comprises ambient air that is displaced into the first volume. According to some embodiments, the ambient air is displaced into the first volume via an opening formed in a fluid tube that extends between and fluidly connects the fluid canister and the wound dressing.

According to some embodiments, the pump is operated to create a first negative pressure within the interior of the first volume, the ambient air being displaced into the first volume in response to operation of the pump being stopped. The first quantity of ambient air is measured based on a first time period during which the first negative pressure within the first volume increases to an ambient pressure.

According to some embodiments, the second volume is measured by operating the pump to entirely fill the second volume with a second quantity of fluid and measuring the volume of the second quantity of fluid. The fluid comprises ambient air that is displaced into the second volume. The ambient air may be displaced into the second volume via the opening formed in the fluid tube.

According to some embodiments, the pump is operated to create a second negative pressure within the interior of the second volume, the ambient air being displaced into the second volume in response to operation of the pump being stopped. The second quantity of ambient air is measured based on a second time period during which the second negative pressure within the second volume increases to ambient pressure.

According to some embodiments, a valve is operably connected to the fluid tube between the opening and the wound dressing. The valve is configured to prevent flow between the fluid canister and the wound dressing at pressures equal to or greater than the first predetermined negative pressure and to permit flow at the second predetermined negative pressure.

According to some embodiments, the pump is operated to create the second negative pressure within the interior of the second volume at a point in time after the operation of the pump to create the first negative pressure within the interior of the first volume. The pump is operated to create the second negative pressure within the interior of the second volume at a point in time prior to the operation of the pump to create the first negative pressure within the interior of the first volume.

In one implementation of the present disclosure, a method for monitoring the progression of the healing of a wound includes operating a pump of a therapy device to measure a first volume of a wound to which a wound dressing in fluid communication with the therapy device is applied. A first quantity of instillation fluid is delivered to the wound via the therapy device based upon the first volume of the wound. Following a first predetermined time period after delivering the instillation fluid, the pump is operated to measure a second volume of the wound. A first rate of healing is calculated based on the difference between the first and second wound volumes and a duration of the first predetermined time period.

According to some embodiments, a second quantity of instillation fluid is delivered to the wound based upon the second volume of the wound. Following a second predetermined time period after delivering the instillation fluid, the pump is operated to measure a third volume of the wound. A second rate of healing is calculated based on the difference between the second and third wound volumes and a duration of the second predetermined time period. The second rate of healing is compared to the first rate of healing. According to some embodiments, a user is alerted if the second rate of healing is less than the first rate of healing.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
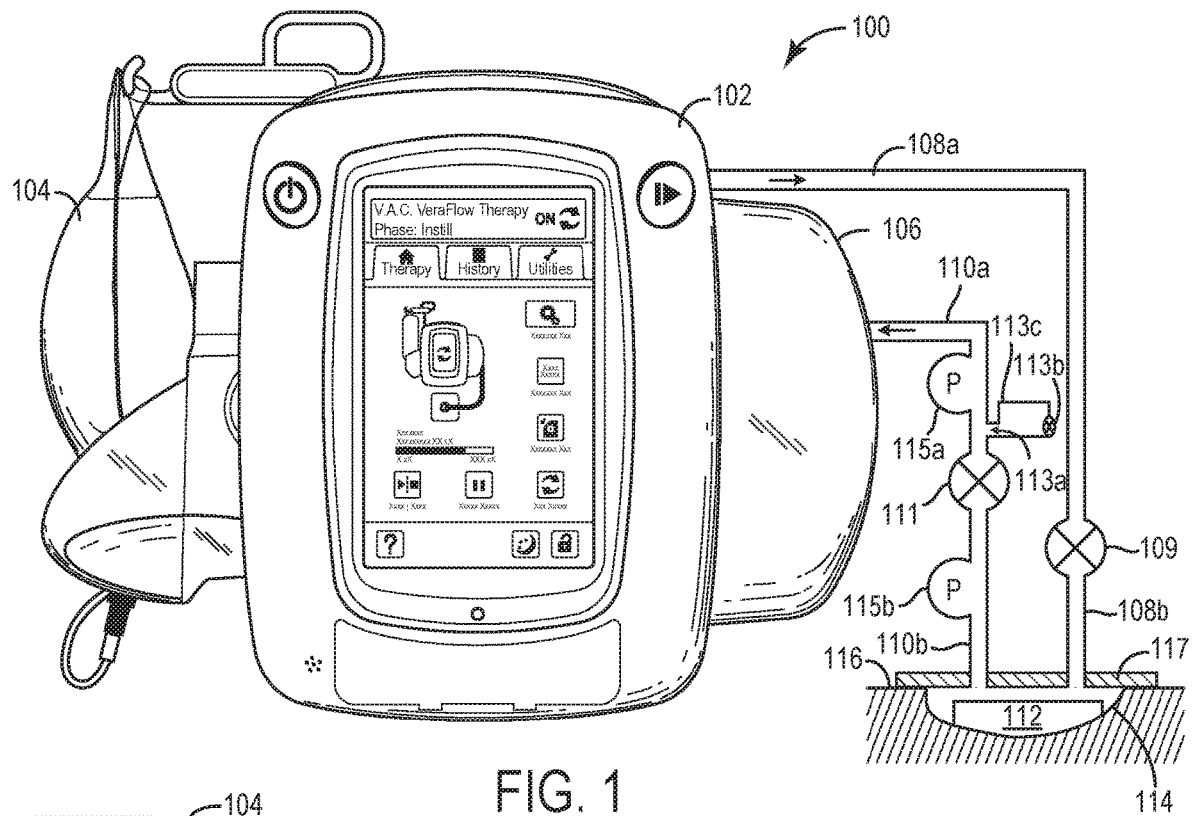
FIG. 1 is a block diagram of a negative pressure wound therapy system including a therapy device coupled to a wound dressing via tubing, according to an exemplary embodiment.

Referring generally to the FIGURES, a wound therapy system is shown according to various exemplary embodiments. The wound therapy system may include a therapy device and a wound dressing. The therapy device may include an instillation fluid canister, a removed fluid canister, a valve, a pneumatic pump, an instillation pump, and a controller. The wound dressing can be applied to a patient's skin surrounding a wound. The therapy device can be configured to deliver instillation fluid to the wound and provide negative pressure wound therapy (NPWT) by maintaining the wound at negative pressure. Components of the wound therapy device, the wound dressing, and the wound site form a negative pressure circuit.

The controller can be configured to operate the pneumatic pump, the instillation pump, and/or other controllable components of the therapy device. In some embodiments, the controller estimates the volume of the wound based on a comparison of observed dynamic pressure responses to negative pressure being applied to the entirety of the negative pressure circuit and negative pressure being applied to a selected portion of the negative pressure circuit. Based on the comparison of the observed dynamic responses, the controller may be configured to determine a quantity of instillation fluid to be delivered to the wound site.

According to some embodiments, the volume relative to the wound site determined by the controller may relate to the dead space at the wound site (i.e. the available space within a drape layer applied about the wound site into which instillation fluid may be delivered). In some such embodiments, the controller may be configured to determine a quantity of instillation fluid to be delivered to the wound site based on a predetermined percentage of the calculated dead space volume at the wound site (e.g., 20%, 50%, 80%, etc.). The controller can then operate the instillation pump to deliver the determined volume of instillation fluid to the wound. By basing the quantity of instillation fluid to be delivered to the wound site on a calculated volume of the dead space at the wound site, the negative pressure system may be configured to provide for more efficient and more precise delivery of instillation fluid, which may reduce the risk of leakage resulting from over-delivery of instillation fluid and the risk of ineffective wound site treatment resulting from under-delivery of instillation fluid.

In some embodiments, the controller may additionally, or alternatively, measure and monitor volumes relative to the wound site at a plurality of times during wound treatment, with the controller determining healing progression of the wound site based on changes in the measured volume relative to the wound site over the course of NPWT treatment. By monitoring the healing progression of the wound site, the controller may be configured to alert a user if the healing of the wound site is not progressing as intended or expected. These and other features of the wound therapy system are described in detail below.

Wound Therapy System

Referring now to FIG. 1, a negative pressure wound therapy (NPWT) system 100 is shown according to an exemplary embodiment. NPWT system 100 is shown to include a therapy device 102 fluidly connected to a wound dressing 112 via tubing 108 and 110. According to various embodiments, a wound dressing 112 may be placed on or within the wound site 114 and adhered or sealed to a patient's skin 116 surrounding a wound site 114 using drape layer 117. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Figure 2:
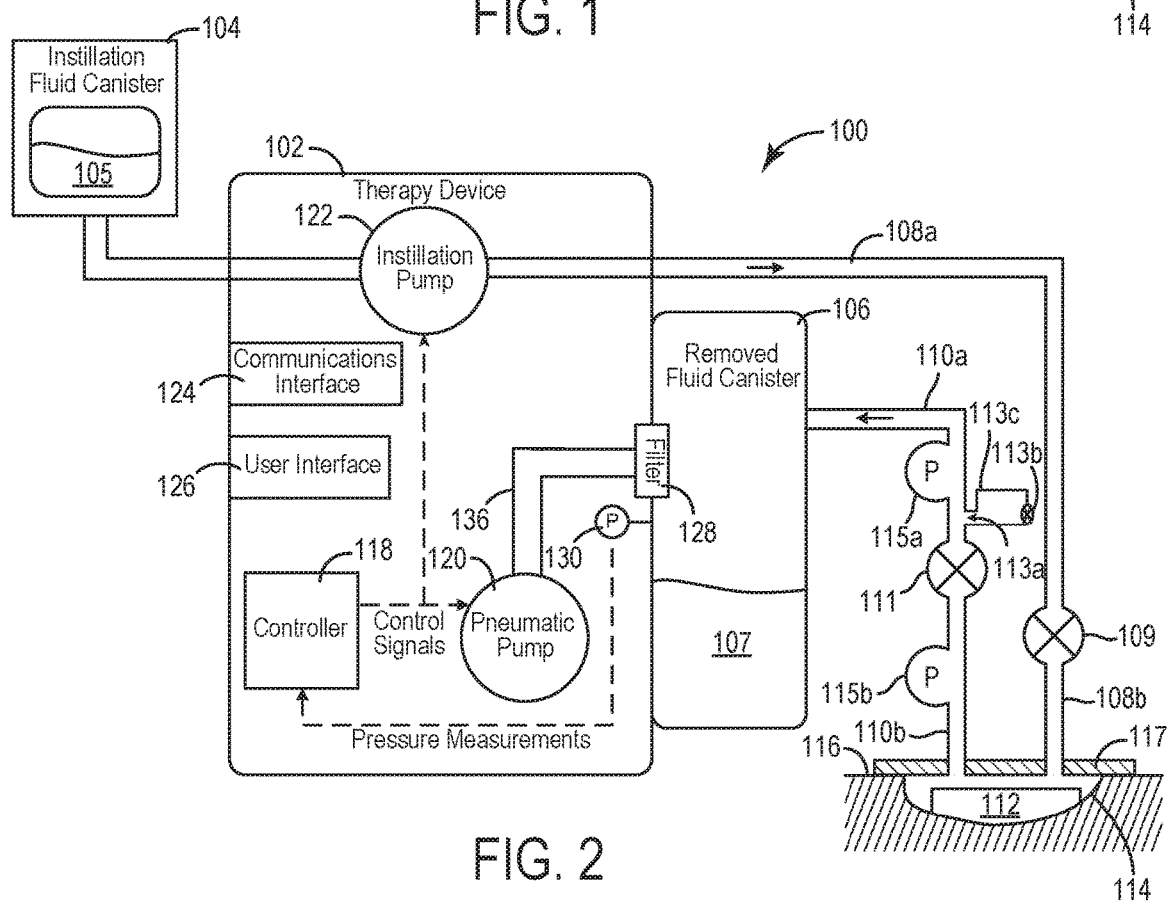
FIG. 2 is a block diagram illustrating the negative pressure wound therapy system of FIG. 1 in greater detail, according to an exemplary embodiment.

As illustrated by the block diagram of FIG. 2, in general the therapy device 102 includes a pneumatic pump 120, an instillation pump 122, a filter 128, and a controller 118. Pneumatic pump 120 can be fluidly coupled to removed fluid canister 106 (e.g., via conduit 136) and can be configured to draw a vacuum within canister 106 by pumping air out of canister 106. In some embodiments, pneumatic pump 120 is configured to operate in both a forward direction and a reverse direction. For example, pneumatic pump 120 can operate in the forward direction to pump air out of canister 106 and decrease the pressure within canister 106. Pneumatic pump 120 can operate in the reverse direction to pump air into canister 106 and increase the pressure within canister 106. Pneumatic pump 120 can be controlled by controller 118, described in greater detail below.

Therapy device 102 can be configured to provide negative pressure wound therapy by reducing the pressure at wound site 114. Therapy device 102 can draw a vacuum at wound site 114 (relative to atmospheric pressure) by removing wound exudate, air, and other fluids from wound site 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids 121 removed from wound site 114 may include instillation fluid 105 previously delivered to wound site 114. Instillation fluid 105 can include, for example, a cleansing fluid, a prescribed fluid, a medicated fluid, an antibiotic fluid, or any other type of fluid which can be delivered to wound site 114 during wound treatment. Instillation fluid 105 may be held in an instillation fluid canister 104 and controllably dispensed to wound site 114 via tubing 108. In some embodiments, installation fluid canister 104 is detachable from therapy device 102 to allow canister 106 to be refilled and replaced as needed.

Installation pump 122 can be fluidly coupled to installation fluid canister 104 via upstream installation tubing 108a and fluidly coupled to wound dressing 112 via downstream installation tubing 108b. Installation pump 122 can be operated to deliver installation fluid 105 to wound dressing 112 and wound site 114 by pumping installation fluid 105 through upstream installation tubing 108a and downstream installation tubing 108b. Installation pump 122 can be controlled by controller 118, described in greater detail below. According to some embodiments, an installation tubing valve 109 valve configured to allow for flow only in the direction from the installation fluid canister 104 to the wound site 114 (e.g. via a one-way valve or a via valve configured to be selectively switched by a user and/or by the controller 118 to a closed position prior to the application of negative pressure to the wound site) may generally be provided at a location along a portion of the downstream installation tubing 108b.

Filter 128 can be positioned between removed fluid canister 106 and pneumatic pump 120 (e.g., along conduit 136) such that the air pumped out of canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound site 114 from therapy device 102).

Removed fluid canister 106 may be a component of therapy device 102 configured to collect wound exudate and other fluids 121 removed from wound site 114. In some embodiments, removed fluid canister 106 is detachable from therapy device 102 to allow canister 106 to be emptied and replaced as needed. A lower portion of canister 106 may be filled with wound exudate and other fluids 107 removed from wound site 114, whereas an upper portion of canister 106 may be filled with air. Therapy device 102 can be configured to draw a vacuum within canister 106 by pumping air out of canister 106. The reduced pressure within canister 106 can be translated to wound dressing 112 and wound site 114 via tubing 110.

As shown in FIG. 1, disposed along tubing 110 at a location between the removed fluid canister 106 and the wound site 114 is a tubing valve 111 configured to selectively permit and prevent fluid flow between the removed fluid canister 106 and the wound site 114. The tubing valve 111 may be defined by any number of different structures (e.g. spring-biased; duck-bill; clamp; check-valve, etc.) configured to allow for the selective control of fluids through the tubing 110, and may include valves that are configured to be selectively opened and/or closed by a user, in response to a sensed stimulus (e.g. a predetermined threshold pressure), or by the controller 118.

Figure 3:
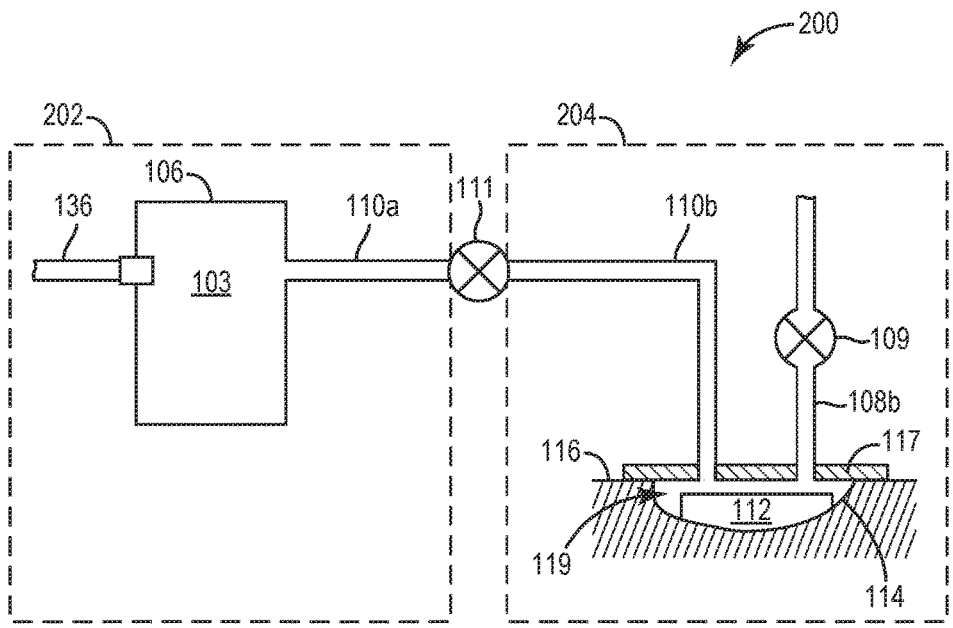
FIG. 3 is a block diagram illustrating the negative pressure circuit, the removed fluid canister circuit and the wound site circuit of the negative pressure wound therapy system of FIG. 1 in greater detail, according to an exemplary embodiment.

Referring to the block diagram of FIG. 3, when the tubing valve 111 is in an open, flow configuration, removed fluid canister 106, tubing 110 (i.e. both upstream tubing portion 110a and downstream tubing portion 110b), conduit 136 extending between pneumatic pump 120 and removed fluid canister 106, the portion of downstream installation tubing 108b extending between the drape layer 117 and installation tubing valve 109, and wound site 114 are fluidly connected to define a negative pressure circuit 200. Referring further to FIG. 3, when the tubing valve 111 is in a closed, no-flow configuration, the removed fluid canister 106, conduit 136 and an upstream tubing portion 110a of the tubing 110 extending between the removed fluid canister 106 and the tubing valve 111 define a removed fluid canister circuit 202 that is fluidly isolated from a wound site circuit 204 defined by the wound site 114, a downstream tubing portion 110b of tubing 110 extending between the tubing valve 111, a portion of downstream installation tubing 108b extending between the drape layer 117 and installation tubing valve 109, and the wound site 114. As will be discussed in more detail below, the volumes of the tubing 110, conduit 136, and portion of downstream installation tubing 108b extending between the drape layer 117 and installation tubing valve 109 define known volumes which can be easily subtracted from or otherwise factored into calculations of volume(s) relative to the wound site 114.

Referring again to FIG. 1, according to some embodiments, also provided along and operably fluidly connected to tubing 110 at a location upstream of tubing valve 111 and downstream of removed fluid canister 106 is a calibrated leak system 113 defined by a vent 113a formed through an outer wall of the tubing 110, the vent 113a being selectively closeable by a vent valve 113b. Also forming a part of calibrated leak system 113 may be a flow detector 113c configured to measure airflow through the vent 113a. As will be described in more detail below, calibrated leak system 113 is configured to selectively control and measure airflow between tubing 110 and the ambient environment surrounding therapy device 102. According to various embodiments, calibrated leak system 113 can be selectively opened to allow airflow into tubing 110 at a known, predetermined rate.

As will be described in more detail below, when both the vent valve 113b and the tubing valve 111 are closed, operation of the pneumatic pump 120 may be configured to draw a vacuum in only the removed fluid canister circuit 202 portion of the negative pressure circuit 200 (such as, e.g. illustrated in FIG. 6E). When the vent valve 113b is closed and the tubing valve 111 is open, operation of the pneumatic pump 120 may be configured to draw a vacuum in the entirety of the negative pressure circuit 200 (such as, e.g., illustrated in FIG. 6C). When the vent valve 113b is open and the tubing valve 111 is closed, airflow from the environment around therapy device 102 may enter through the vent 113a of the calibrated leak system 113 and fill the vacuum within the removed fluid canister circuit 202 (such as, e.g., illustrated in FIG. 6F). As illustrated, e.g. by FIG. 6D, when both the vent valve 113b and the tubing valve 111 are open, airflow from the environment around therapy device 102 may enter through the vent 113a of the calibrated leak system 113 and fill the vacuum within the entirety of the negative pressure circuit 200.

Figure 4:
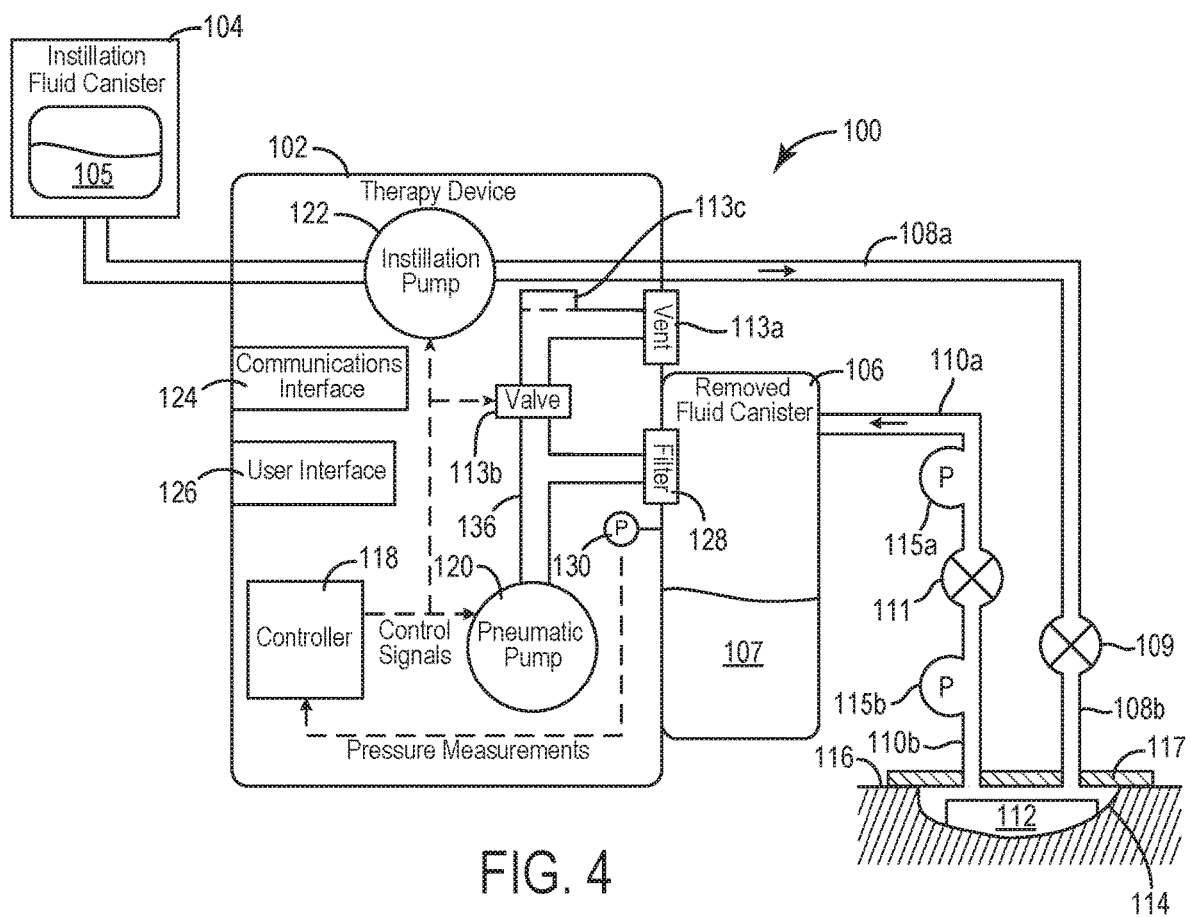
FIG. 4. is a block diagram illustrating a negative pressure wound therapy system, according to an exemplary embodiment

Although the calibrated leak system 113 has been disclosed as being positioned in-line with a portion of the tubing 110 extending between the wound site 114 and the removed fluid canister 106, according to some embodiments, such as, e.g., illustrated in FIG. 4, the calibrated leak system 113 may be instead formed in-line with conduit 136. The operation of the calibrated leak system 113 of the embodiment of FIG. 4 is similar to the operation of the calibrated leak system 113 illustrated in FIG. 1, with the calibrated leak system 113 of FIG. 4 being configured to provide a path through which air from the ambient environment may flow into and fill portions or the entirety of the negative pressure circuit 200 following the creation of a vacuum within a portion or entirety of the negative pressure circuit 200. As will be understood, according to various embodiments, any of the methods or systems illustrated or disclosed herein which incorporate a calibrated leak system 113 embodiment as illustrated in FIG. 1 may be modified with a calibrated leak system 113 embodiment as illustrated in FIG. 4.

As illustrated by the block diagram of FIG. 2, according to various embodiments, the controller 118 may be configured to operate various components of therapy device 102. In particular, as will be described in more detail below, according to various embodiments, the controller 118 may be configured to control the various components of the NPWT system 100 to execute one or more volume determination procedures via which, e.g. a quantity of instillation fluid 105 to be delivered to the wound site 114 may be determine, the healing progression of the wound site may be tracked, etc. According to various embodiments, the controller 118 may be configured such that these procedures may be performed with minimal user intervention and/or input.

According to various embodiments, therapy device 102 may include a variety of sensors. For example, in some embodiments, therapy device 102 may include pressure sensor 115a and/or 115b located in-line in the upstream tubing portion 110a and/or downstream tubing portion 110b, which are configured to measure pressure at the removed fluid canister 106 and/or wound site 114. Pressure measurements recorded by pressure sensor(s) 115a and/or 115b can be communicated to controller 118. According to various embodiments, controller 118 may use the pressure measurements from pressure sensor(s) 115a and/or 115b as inputs to various pressure testing operations and control operations performed by controller 118.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. User interface 126 can also display alerts generated by controller 118. For example, controller 118 can generate a "no canister" alert if canister 106 is not detected.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

Methods of Use

Figure 5:
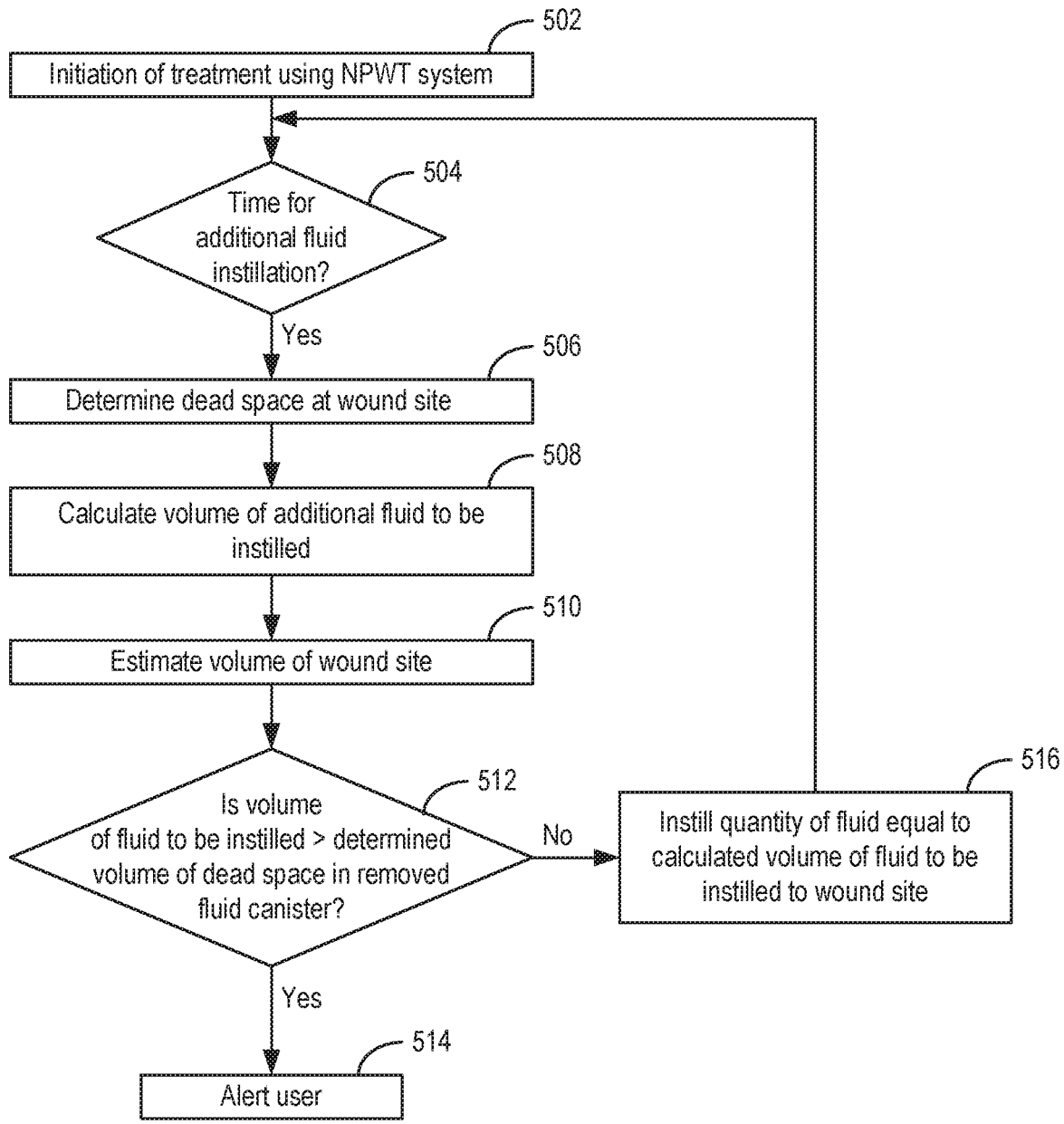
FIG. 5 is a flowchart of a method of using a negative pressure wound therapy system, according to an exemplary embodiment.

Referring to FIG. 5, a flowchart of a method 500 of using NPWT system 100 according to an exemplary embodiment is shown. As will be discussed in more detail with reference to FIGS. 6A-6G, initial set up of the NPWT system 100 and a delivery of an initial amount of instillation fluid 105 to a wound site 114 being treated by the NPWT system 100 occurs at step 502.

As shown at step 504, according to various embodiments, it may be desirable to deliver additional instillation fluid 105 to the wound site 114 following the instillation of an initial amount of instillation fluid 105 to the wound site 114. As will be understood, the determination at step 504 of when and if additional instillation fluid 105 is to be delivered to the wound site 114 may be based on any number of various factors, including e.g. elapsed time from a prior instillation; type of wound site 114; desired course of wound site 114 treatment; sensed conditions related to the wound site 114, etc., and may be decided automatically by the controller 118, or may be based on user input.

If it is determined at step 504 that additional fluid is to be delivered, at step 506 the dead space 119 at the wound site 114 is determined according to any of the methods as will be described below. According to various embodiments (described in more detail below), at step 506, the controller 118 may be configured to determine the dead space at the wound site 114 prior to such delivery of additional instillation fluid 105, irrespective of: whether the quantity of instillation fluid 105 previously instilled to the wound site 114 is known; the presence of non-absorbed instillation fluid 105 and/or wound exudate in the space defined between the wound site 114 and the drape layer 117; whether the volume of any contents 107 in the removed fluid canister 106, the volume of the removed fluid canister 106 itself, and/or the volume of any contents 107 previously emptied from the removed fluid canister 106 are known; whether the removed fluid canister 106 has been replaced with a different-sized removed fluid canister 106 during the course of the NPWT treatment; changes to the shape/size/volume of the wound site 114; etc.

At step 508, the quantity of additional instillation fluid 105 to be delivered to the wound site 114 is calculated. According to various embodiments, the quantity of additional instillation fluid 105 delivered to the wound site 114 may be based on the volume of the dead space determined at step 506. For example, in some embodiments, the controller 118 may calculate the volume of instillation fluid 105 to be delivered to wound site 114 by multiplying the volume if dead space determined at step 506 by a fluid instillation factor. The fluid instillation factor may be equal to or less than one (i.e., between zero and one) such that the volume of instillation fluid 105 delivered to the wound site 114 does not exceed the available space within the drape layer 117 (i.e. dead space), thereby minimizing the risk of inadvertent leakage from the wound dressing 112/drape layer 117. In some embodiments, the fluid instillation factor is between approximately 0.2 and approximately 0.8.

In addition to being used to calculate instillation fluid 105 volumes, in some embodiments, the NPWT may be additionally, or alternatively, used to monitor and track the progress of healing of the wound site 114 over time. Accordingly, in some embodiments, method 500 may optionally include the step 510 of estimating wound site 114 volume, and using the estimated volume to track healing progress of the wound site 114, discussed in more detail with reference to FIG. 11 below.

In some embodiments, it may be desired to remove instillation fluid 105 previously instilled to a wound site 114 from the wound site 114 at some time following the delivery of the instillation fluid 105 to the wound site 114. Accordingly, it may be advantageous to confirm, prior to instilling instillation fluid 105 to the wound site 114, that the dead space in the removed fluid canister 106 will be sufficient to receive the removed instillation fluid 105 and/or any additional fluid 121 (e.g. wound exudate) from the wound site 114 prior to delivering the additional instillation fluid 105 to the wound site 114. As such, method 500 may optionally include step 512 at which the volume of additional instillation fluid 105 calculated at step 508 is compared to the dead space of the removed fluid container 106 (measured, e.g., during the determination of dead space at the wound site 114 at step 506), with an alarm being presented to the user at step 514 if the instillation fluid 105 to be delivered exceeds the dead space of the removed fluid canister 106. If the instillation fluid 105 to be delivered does not exceed the dead space of the removed fluid canister 106 (or if step 512 is not included as part of method 500), the calculated instillation fluid 105 is delivered to the wound site 114, with some or all of steps 504, 506, 508, 510, 512, 514, 516 being repeated any number of additional times over the course of the NPWT treatment.

Figure 6A:
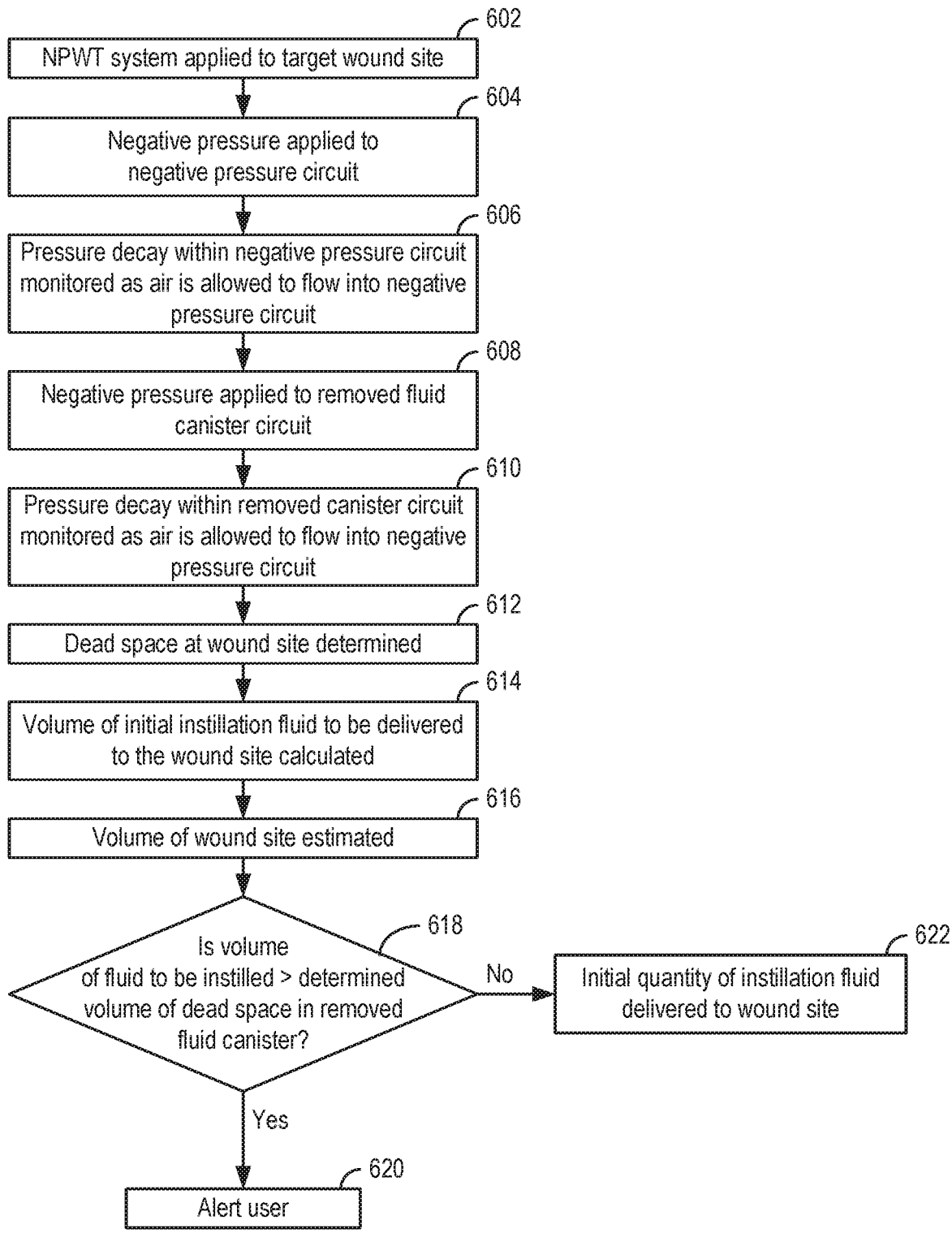
FIG. 6A is a flowchart of method of instilling an initial quantity of fluid to a wound site using the negative pressure wound therapy system, according to an exemplary embodiment.
Figure 6B:
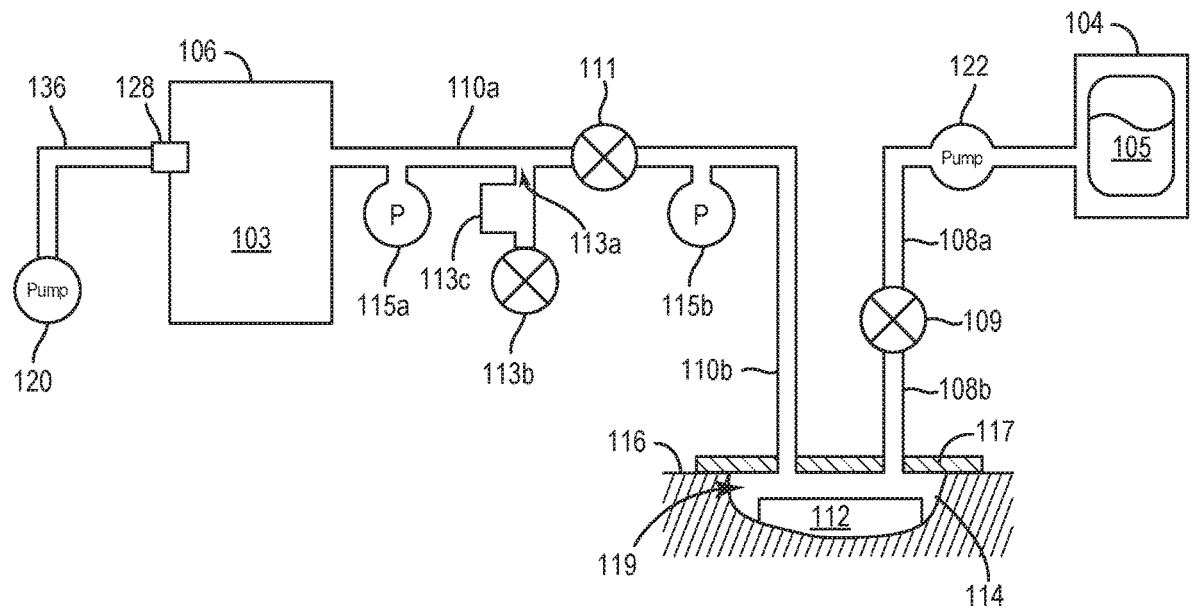
FIG. 6B illustrates a negative pressure wound therapy system applied to a desired wound site to be treated, prior to the instillation of an initial volume of fluid to the wound site according to an exemplary embodiment.

Referring to FIG. 6A a flowchart detailing the steps of a method 600 for an initial set up of NPWT system 100 and for delivery of an initial amount of instillation fluid 105 to a wound site 114 entailed in step 502 of the method 500 of FIG. 5 is shown according to one embodiment. At step 602, a NPWT system 100 (such as, e.g., illustrated in FIG. 1) is provided, with the drape layer 117 and wound dressing 112 being positioned at the desired wound site 114 to be treated, as shown, e.g. in FIG. 6B.

Figure 6C:
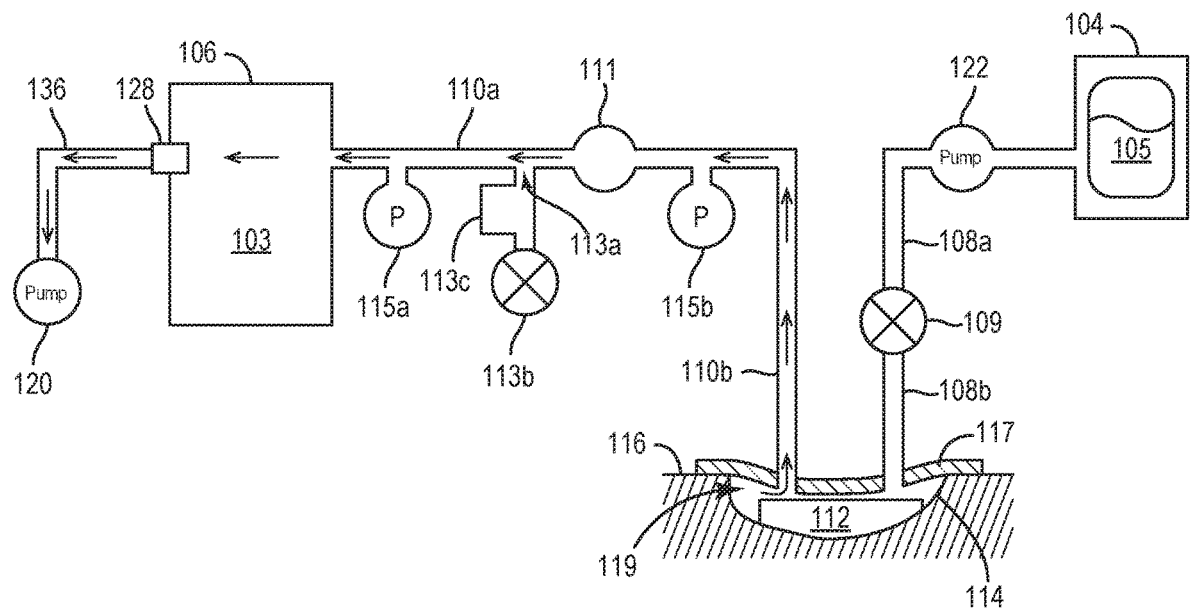
FIG. 6C illustrates the negative pressure wound therapy system of FIG. 6B following an application of a first negative pressure to the negative pressure wound therapy system, according to an exemplary embodiment.

Once the set-up of the NPWT system 100 at step 502 is complete, the determination of the dead space 119 available at the wound site 114 into which instillation fluid 105 may be delivered may begin at step 604 with the controller 118 operating the pneumatic pump 120 to establish a first desired negative pressure within the entirety of the negative pressure circuit 200, such as, e.g., illustrated in FIG. 6C.

In embodiments in which the tubing valve 111 comprises a normally-closed pressure sensitive valve that is openable in response to an applied, predetermined threshold negative pressure, the first desired negative pressure generated by the controller 118 at step 604 may be equal to or greater than the predetermined threshold pressure required to open the tubing valve 111, so as to ensure that the vacuum applied by the pneumatic pump 120 is applied across the entirety of the negative pressure circuit 200. In some embodiments, the threshold pressure required to open the tubing valve 111 may be a pressure of approximately negative 125 mmHg, with the controller 118 being configured to apply at step 604 a first negative pressure that is equal to or greater than negative 125 mmHg.

Alternatively, in embodiments in which the opening/closing of the tubing valve 111 is controlled manually or in direct response to a signal from the controller 118, the negative pressure delivered at step 604 may generally include any desired range of negative pressures, with step 604 including verification by the user and/or controller that the tubing valve 111 is in an open, flow orientation prior to the negative pressure being applied by the pneumatic pump 120. As illustrated, e.g. in FIG. 6C, according to various embodiments, the instillation tubing valve 109 and the vent valve 113b may be configured to be set to closed configurations during the application of negative pressure to the negative pressure circuit 200.

Figure 6D:
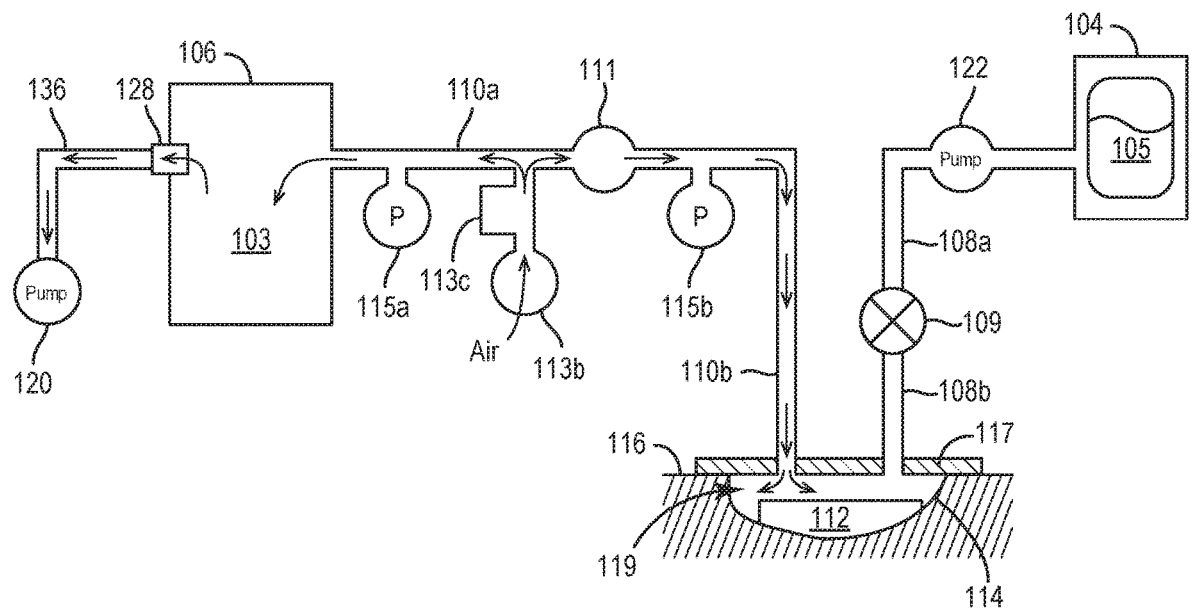
FIG. 6D illustrates the negative pressure wound therapy system of FIG. 6C during venting of the negative pressure wound therapy system following the application of the first negative pressure as shown in FIG. 6C, according to an exemplary embodiment.

As illustrated by FIG. 6D, at step 606, following the attainment of the desired first negative pressure within the negative pressure circuit 200 (as, e.g., measured and reported to the controller 118 by pressure sensor 115a and/or pressure sensor 115b), the operation of the pneumatic pump 120 is stopped, and the vent valve 113b is opened to allow air from the ambient environment surrounding the therapy device 102 to flow through the vent 113a and into the negative pressure circuit 200. According to various embodiments, the opening of the vent valve 113b at step 606 may be effectuated manually by a user or in response to instructions from the controller 118. In yet other embodiments, the calibrated leak system 113 may be formed without a vent valve 113b (i.e. the vent 113a defines a constant leak within the tubing 110), such that air from the ambient environment surround the therapy device 102 will flow into the negative pressure circuit 200 without requiring any user and/or controller 118 intervention.

As air from the ambient environment flows in to the negative pressure circuit 200, parameters related to the flow of air through the vent 113a into the negative pressure circuit 200 are monitored (e.g. via flow detector 113c, pressure sensor 115a, pressure sensor 115b, etc.), with the measured parameters subsequently being used by the controller 118 at step 612 to determine the volume of the negative pressure circuit 200. According to various embodiments, the parameters related to the flow of air into the negative pressure circuit 200 may include, e.g. the rate of flow of air into the negative pressure circuit 200 (as measured, e.g., by flow detector 113c), the duration of time required for pressure within the negative pressure circuit 200 to increase to a predetermined pressure (e.g. ambient pressure) following the opening of the vent 113a and/or following operation of the pump 120 being ceased, the changing pressure (as, e.g. measured by pressure sensor 115a and/or pressure sensor 115b) within the negative pressure circuit 200 as the pressure increases from the negative pressure applied at step 604 to the predetermined pressure, etc.

Figure 6E:
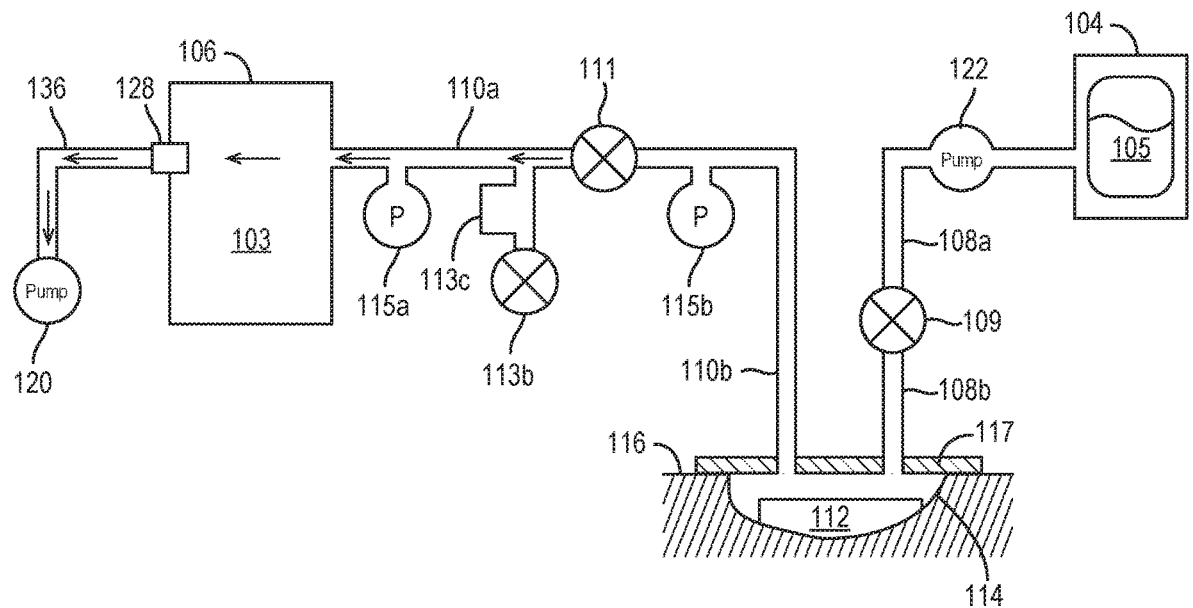
FIG. 6E illustrates the negative pressure wound therapy system of FIG. 6B following an application of a second negative pressure to the negative pressure wound therapy system, according to an exemplary embodiment.

Once the pressure within the negative pressure circuit 200 has increased to a desired pressure and the measurement of the desired parameters has been completed by the controller 118, the controller 118 may be configured operate pneumatic pump 120 to establish a second desired negative pressure within the removed fluid canister circuit 202 portion of the negative pressure circuit 200 at step 608, such as, e.g. illustrated in FIG. 6E. In embodiments in which the tubing valve 111 comprises a normally-closed pressure sensitive valve that is openable in response to an applied, predetermined threshold negative pressure, the second desired negative pressure generated by the controller 118 at step 608 may be less than the predetermined threshold pressure required to open the tubing valve 111, so as to ensure that the vacuum applied by the pneumatic pump 120 at step 608 is applied across only the removed fluid canister circuit 202 portion of the negative pressure circuit 200. For example, in some embodiments, the threshold negative pressure required to open the tubing valve 111 may be approximately negative 125 mmHg, with the controller 118 being configured to apply a negative pressure at step 608 that is less than negative 125 mmHg, such as, e.g. a pressure of approximately negative 50 mmHg.

Alternatively, in embodiments in which the opening/closing of the tubing valve 111 is controlled manually or in direct response to a signal from the controller 118, the negative pressure delivered at step 608 may generally include any desired range of negative pressures, with step 608 including verification by the user and/or controller that the tubing valve 111 is in a closed, no-flow orientation prior to the negative pressure being applied by the pneumatic pump 120. As will be understood, in such embodiments, the second negative pressure applied by the controller 118 at step 608 to the removed fluid canister circuit 202 may include a pressure that is equal to or different from the negative pressure that is applied by the controller 118 at step 604 to the negative pressure circuit 200. As illustrated, e.g. in FIG. 6E, according to various embodiments, the instillation tubing valve 109 and the vent valve 113b may be configured to be set to closed configurations during the application of negative pressure to the removed fluid canister circuit 202 at step 608.

Figure 6F:
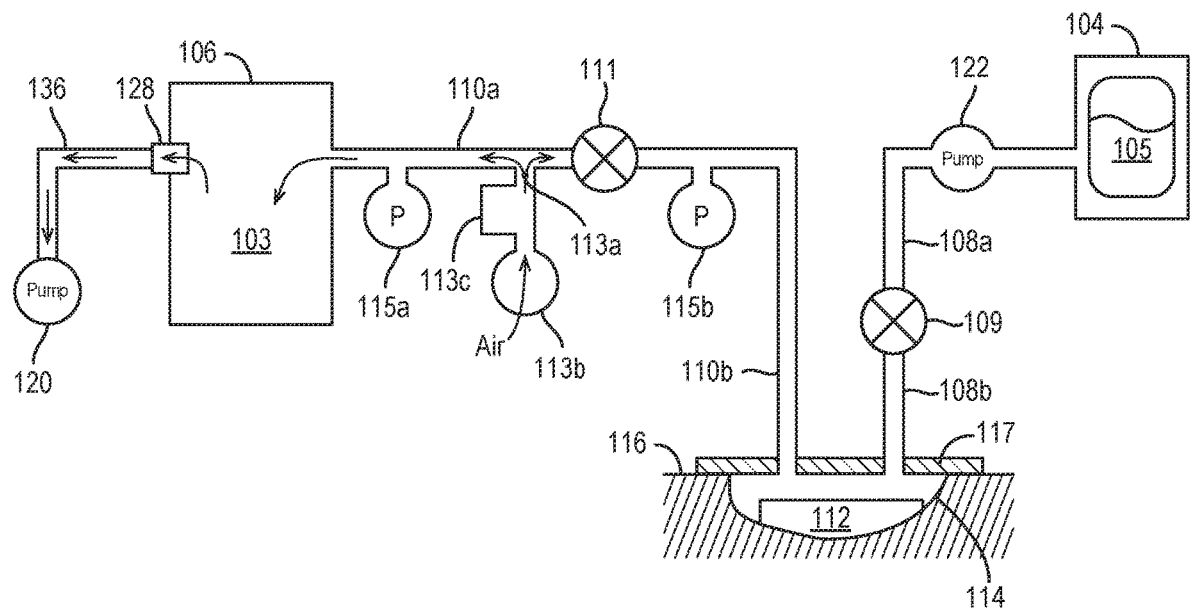
FIG. 6F illustrates the negative pressure wound therapy system of FIG. 6E during venting of the negative pressure wound therapy system following the application of the second negative pressure as shown in FIG. 6E, according to an exemplary embodiment.
Figure 6G:
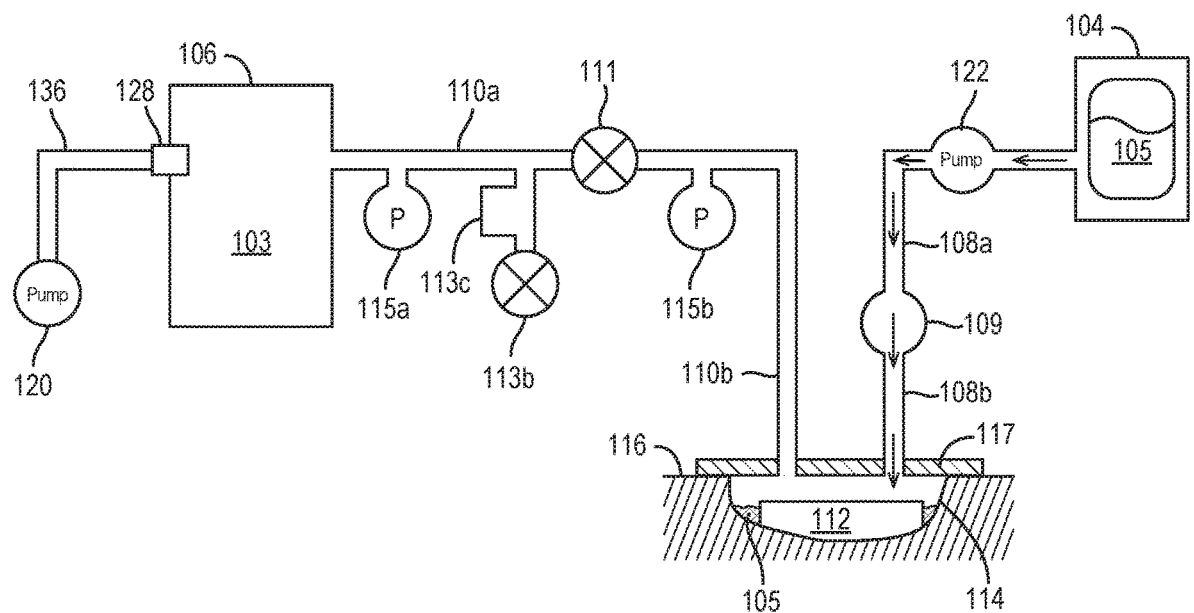
FIG. 6G illustrates the installation of fluid to the wound site using the wound therapy system of FIG. 6B, according to an exemplary embodiment.

As illustrated by FIG. 6F, at step 610, following the attainment of the desired second negative pressure within the removed fluid canister circuit 202 (as, e.g., measured and reported to the controller 118 by pressure sensor 115a and/or pressure sensor 115b), the operation of the pneumatic pump 120 is stopped, and air from the ambient environment surrounding the therapy device 102 is allowed to flow through the vent 113a and into the removed fluid canister circuit 202. As air from the ambient environment flows into the removed fluid canister circuit 202, parameters related to the flow of air through the vent 113a and into the removed fluid canister circuit 202 are monitored, with the measured parameters subsequently being used by the controller 118 to calculate the volume of the removed fluid canister circuit 202 at step 612. According to various embodiments, the parameters related to the flow of air into removed fluid canister circuit 202 may include, e.g. the rate of flow of air into the removed fluid canister circuit 202 (as measured, e.g., by flow detector 113c), the duration of time required for pressure within the removed fluid canister circuit 202 to increase to a predetermined pressure (e.g. ambient pressure) following the opening of the vent 113a and/or ceasing operation or the pump 120 at step 610, the pressure (as, e.g. measured by pressure sensor 115a and/or pressure sensor 115b) within the removed fluid canister circuit 202 as the pressure increases from the negative pressure applied at step 608 to the predetermined pressure; etc.

At step 612, the controller 118 may be configured to determine the volumes of the removed fluid canister circuit 202 and the negative pressure circuit 200 based on the parameters measured at steps 606 and 610. According to some embodiments, the controller 118 may base these volume calculations on stored relationships between various measured parameter values and corresponding volumes. These relationships between measured parameter measurements and corresponding volumes that are stored by the controller 118 may include various functions, models, lookup table, etc., and may be based on pre-existing information input and stored by the controller 118, or on information obtained and processed by the controller 118 during an optional, initial training procedure conducted by the controller 118 prior to the use of the NPWT system 100 to treat wound site 114 (e.g. prior to the initiation of method 500; as part of the initial setup and initial instillation of instillation fluid of step 502; etc.). One non-limiting examples of embodiments of training procedures by which such relationships may be generated by the controller 118 are outlined in related, co-pending U.S. Provisional Application 62/650,132, filed Apr. 17, 2018 and titled WOUND THERAPY SYSTEM WITH WOUND VOLUME ESTIMATION, the entire disclosure of which is incorporated by reference herein.

Using the determined volumes of the removed fluid canister circuit 202 and the negative pressure circuit 200, the controller 118 may determine the volume of the dead space 119 at the wound site 114 (i.e. the portion of the interior space defined between the wound site 114 and the lower surface of the drape layer 117 that is not occupied by the wound dressing 112 and/or any instillation fluid 105/other fluid) by subtracting the volume of the removed fluid canister circuit 202 from the volume of the negative pressure circuit 200. According to various embodiments, the determination of the volume of the dead space 119 at the wound site 114 at step 614 may also include subtracting or otherwise adjusting the calculated difference between the volumes of the removed fluid canister circuit 202 and the negative pressure circuit 200 to account for/factor in the known volumes of the downstream tubing portion 110b and the portion of the downstream instillation tubing 108b extending between the drape layer 117 and the instillation tubing valve 109 into the determination of the volume of the dead space 119 at the wound site 114.

At step 614, an initial quantity of instillation fluid 105 that is to be delivered to the wound site 114 is calculated. According to various embodiments, the calculated initial quantity of instillation fluid 105 that is delivered to the wound site 114 may be based on the volume of the dead space 119 calculated by the controller 118 at step 612. For example, in some embodiments, the controller 118 may calculate the initial volume of instillation fluid 105 to be delivered to the wound site 114 by multiplying the volume of dead space 119 calculated at step 612 by a fluid instillation factor. The fluid instillation factor may be equal to or less than one (i.e., between zero and one) such that the volume of instillation fluid 105 delivered to the wound site 114 does not exceed the available space within the drape layer 117 (thereby minimizing inadvertent leakage from the wound dressing 112/drape layer 117. In some embodiments, the fluid instillation factor is between approximately 0.2 and approximately 0.8. However, it is contemplated that the fluid instillation factor can have any value in various alternative embodiments.

As noted previously with reference to step 510, in addition to being used to calculate a quantity of instillation fluid 105 to be delivered during any stage of treatment using NPWT system 100 and under any number of different conditions (e.g. allowing for the calculation of additional instillation fluid 105 to be delivered at step 516 even if the removed fluid canister 106 has been emptied, or entirely replaced with a different sized removed fluid canister 106 during the course of treatment), in some embodiments the NPWT system 100 may be additionally, or alternatively, used to monitor and track the progress of healing of the wound site 114 over time. Accordingly, in some embodiments, at step 616, an initial baseline wound site 114 volume estimate may optionally be determined (via, e.g. a method as described with regards to FIG. 11 below) and stored by the controller 118, which may be used as a reference point against which future wound site 114 volume estimates may be compared to track healing progression of the wound site 114.

For reasons similar to those described with reference to step 512 of the method 500 of FIG. 5, according to some embodiments, at step 618 the amount of initial instillation fluid 105 that is to be delivered calculated at step 614 may be compared to a determined dead space 103 of the removed fluid canister 106 to determine whether the dead space within the removed fluid canister 106 will be sufficient to collect any fluids 121 from the wound site 114 (including non-absorbed instillation fluid 105) following the delivery of instillation fluid 105 at step 516. As will be understood, in embodiments in which the NPWT system 100 has not been operated prior to the use of the NPWT system 100 at step 602, the volume of the removed fluid canister 106 should be empty, such that the dead space 103 of the removed fluid container 106 should be equal to the volume of the removed fluid canister 106. If the volume of the removed fluid canister 106 is not known and/or if removed fluid 107 is present in the removed fluid canister 106 at step 602, the dead space 103 of the removed fluid container may be calculated by subtracting the known volumes of conduit 136 and the upstream tubing portion 110a from the volume of the removed fluid canister circuit 202 determined at step 614. Similar to step 514, at step 620 an alarm may be presented to a user if the initial volume of instillation fluid 105 to be delivered calculated at step 614 exceeds the dead space 103 of the removed fluid canister 106. Otherwise, if the volume of the initial instillation fluid 105 to be delivered does not exceed the dead space 103 of the removed fluid canister 106, the calculated instillation fluid 105 is delivered to the wound site 114 at step 622, as shown, e.g. in FIG. 6F.

Figure 7:
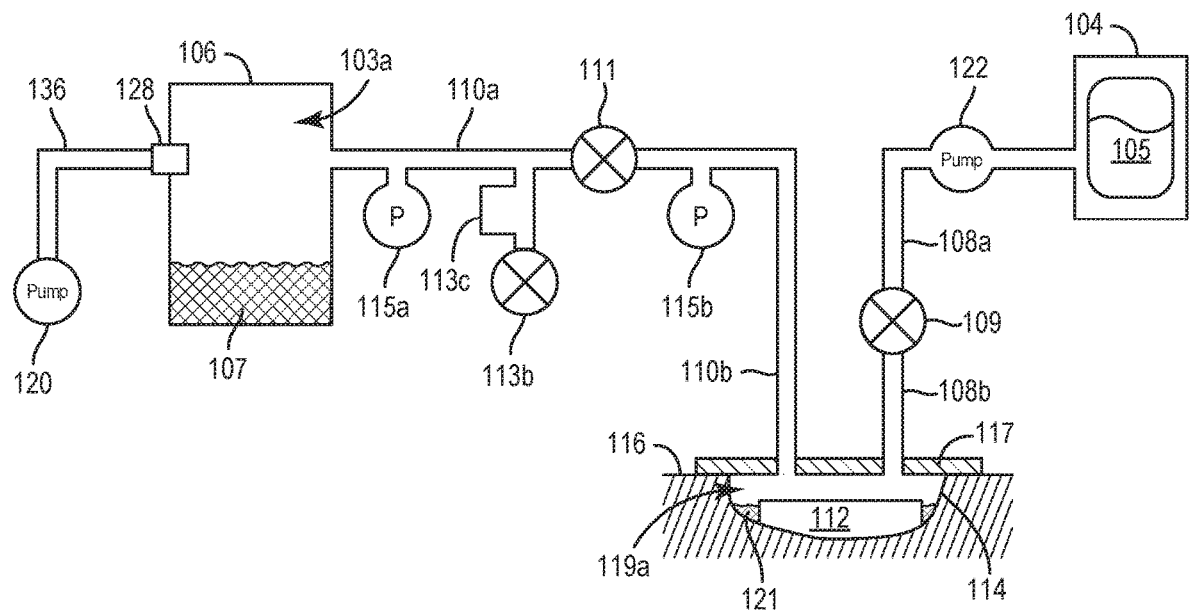
FIG. 7 illustrates a negative pressure wound therapy system applied to a wound site following an initial instillation of fluid to the wound site, according to an exemplary embodiment.

Referring to FIG. 7, a NPWT system 100 according to one embodiment is shown at a point in time subsequent to a decision to instill additional instillation fluid 105 to the wound site 114 at step 504 of the method 500 of FIG. 5, but prior to the determination of wound dead space at the wound site at step 506. As shown in FIG. 7, at the time immediately preceding the determination of dead space at the wound site 114 at step 506, a quantity of fluid 121 (e.g. non-absorbed instillation fluid 105 from a prior instillation, wound exudate, etc.) may be present in the space between the drape layer 117 and the wound site 114, with the remaining space between the drape layer 117 and the wound site 114 defining an initial dead space 119a. As also shown in FIG. 7, according to some embodiments, an initial quantity of removed fluid 107 may be present in the removed fluid canister 106 at the time immediately preceding the start of step 506, with the remaining volume of the removed fluid canister 106 being defined by an initial dead space 103a. As will be understood, according to some embodiments, no fluid may be present at either the wound site 114 and/or in the removed fluid canister 106 at the time immediately preceding step 506, in which embodiments the quantities of each of the fluid 121 in the wound space and the removed fluid 107 in the removed fluid canister 106 would be equal to zero.

As noted above, a quantity of fluid 121 may be present at the wound site 114 immediately prior to the initiation of step 506. According to some embodiments, it may not be desired and/or required to remove fluid 121 from the wound site (e.g. non-absorbed instillation fluid 105 from prior instillations, wound exudate, etc.) prior to the delivery of additional instillation fluid 105 to the wound site 114 at step 516 of the method 500 of FIG. 5. Accordingly, in some embodiments of method 500, the additional instillation fluid 105 instilled to the wound site at step 516 may be delivered to the wound site 114 irrespective of any fluid 121 that may be present at the wound site 114.

Referring to FIGS. 8A-8E, one embodiment of a method 800 of determining an amount of dead space at a wound site 114 which may be used at step 506 of the method 500 of FIG. 5 in embodiments in which fluid 121 from the wound site 114 is not removed from the wound site 114 prior to instilling additional instillation fluid 105 is illustrated. In particular, according to the method 800 of FIGS. 8A-8E, as no fluid 121 is displaced from the wound site 114 during the method 800 (i.e. step 506), the final dead space into which the additional instillation fluid 121 will be instilled will be the same initial dead space 119a at the wound site that is present immediately prior to the initiation of step 506 (i.e. the dead space 119a shown in FIG. 7).

Figure 8A:
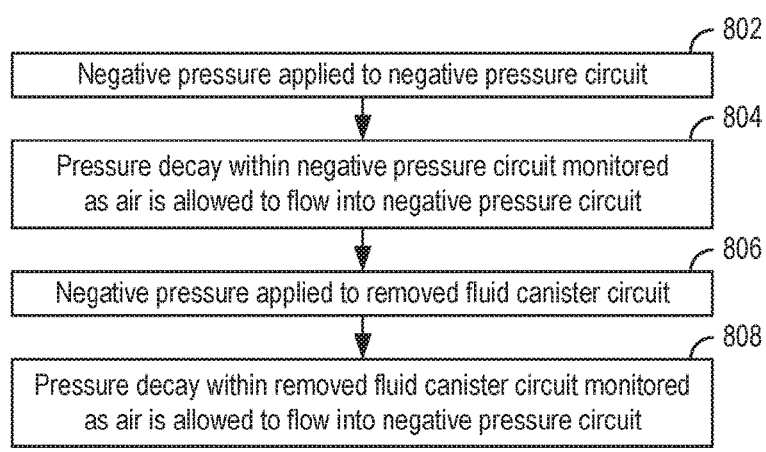
FIG. 8A is a flowchart of method of instilling an additional quantity of fluid to a wound site using the negative pressure wound therapy system of FIG. 7, according to an exemplary embodiment.
Figure 8B:
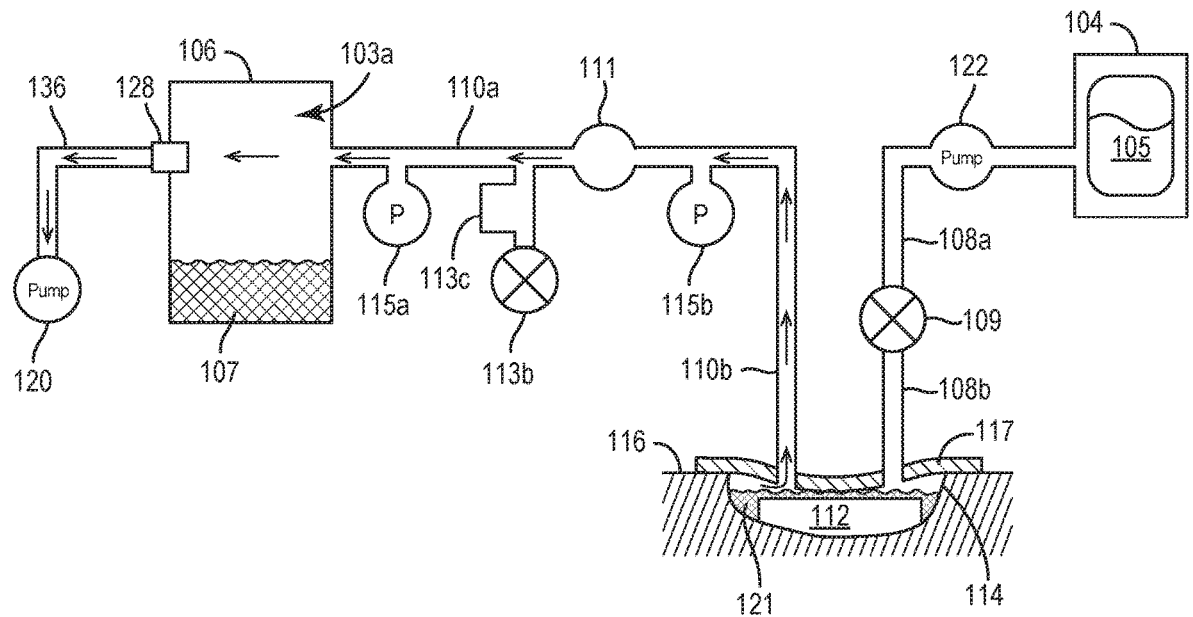
FIG. 8B illustrates the negative pressure wound therapy system of FIG. 7 following an application of a first negative pressure to the negative pressure wound therapy system, according to an exemplary embodiment.
Figure 8C:
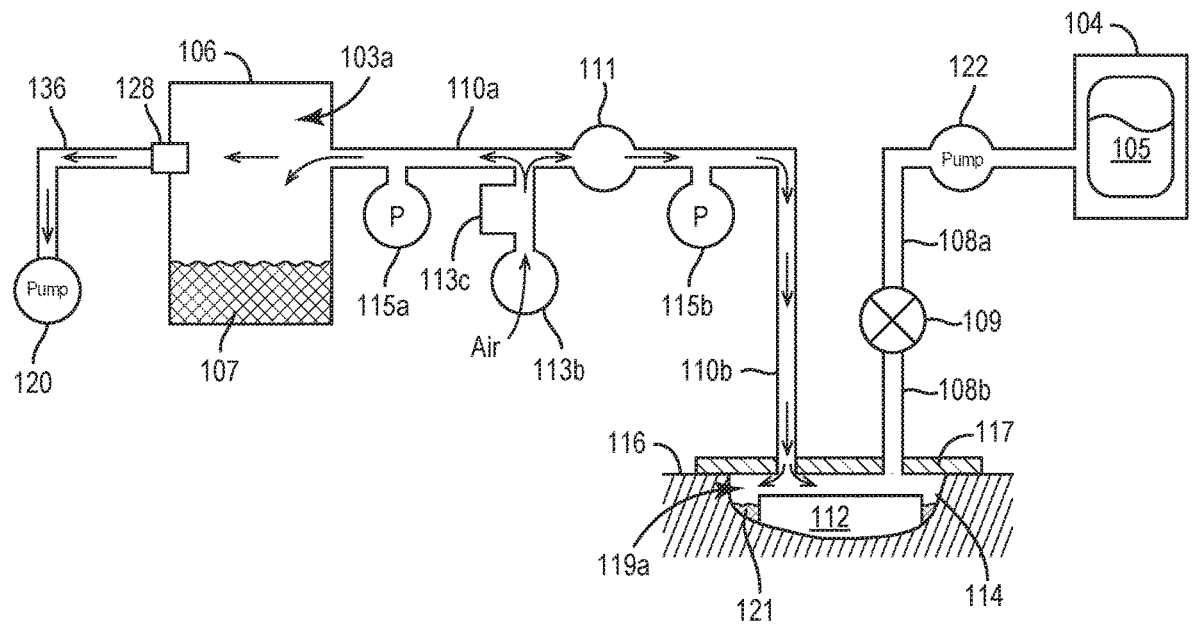
FIG. 8C illustrates the negative pressure wound therapy system of FIG. 8B during venting of the negative pressure wound therapy system following the application of the first negative pressure as shown in FIG. 8B, according to an exemplary embodiment.
Figure 8D:
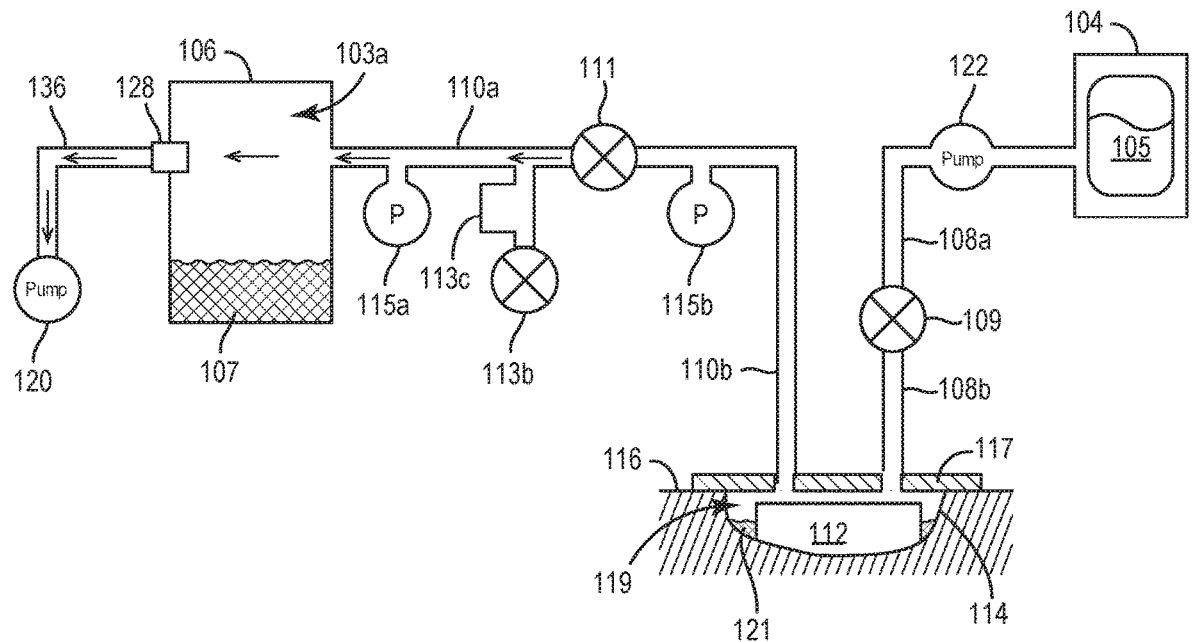
FIG. 8D illustrates the negative pressure wound therapy system of FIG. 7 following an application of a second negative pressure to the negative pressure wound therapy system, according to an exemplary embodiment.
Figure 8E:
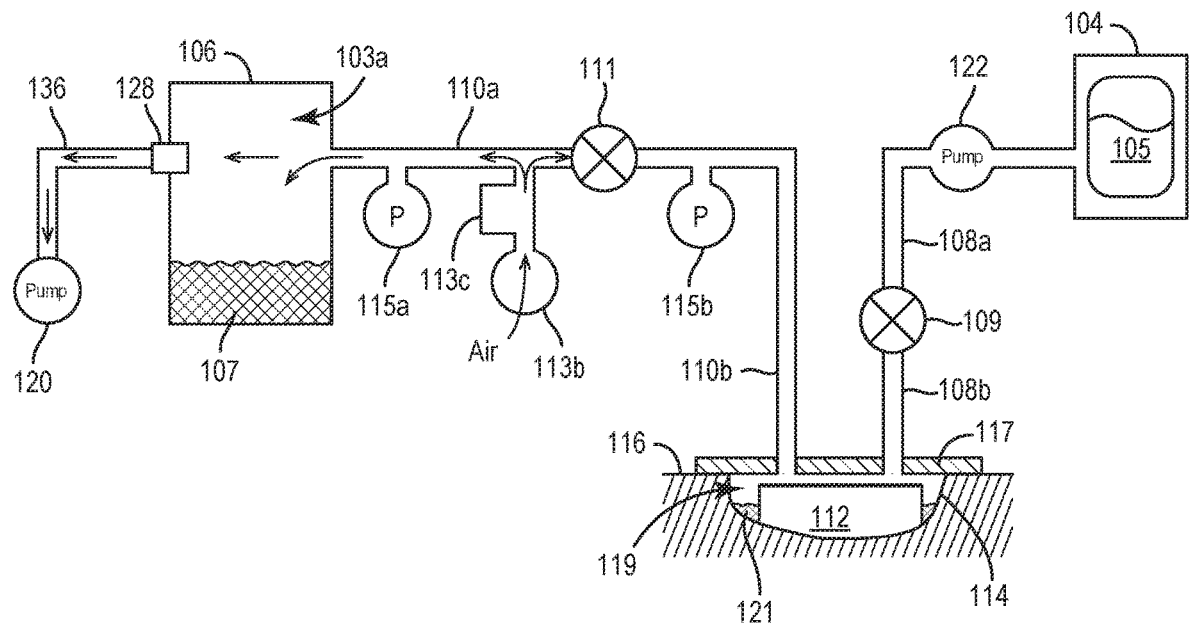
FIG. 8E illustrates the negative pressure wound therapy system of FIG. 8D during venting of the negative pressure wound therapy system following the application of the first negative pressure as shown in FIG. 8D, according to an exemplary embodiment.

As shown by the flowchart in FIG. 8A, the method 800 of determining dead space is substantially the same as the method 600 of calculating the dead space 119 upon initial instillation of instillation fluid 105 to the wound site 114 at step 502 (which is discussed in more detail with reference to FIGS. 6A-6G). In particular, similar to steps 604 and 606, the method 800 of FIG. 8A also includes steps 802 and 804 (shown, e.g. in FIGS. 8B and 8C, respectively) during which negative pressure is applied to and removed from the negative pressure circuit 200. Similar to steps 608 and 610 of the method 600 of FIG. 6A, the method 800 of FIG. 8 also includes steps 806 and 808 (shown, e.g. in FIGS. 8D and 8E, respectively) during which negative pressure is applied to and removed from the removed fluid canister circuit 202. Also similar to the method 600 of FIG. 6A, in the method 800 of FIGS. 8A-8E, the application and subsequent removal of negative pressure to the negative pressure circuit 200 of steps 802 and 804 may be performed either prior to or after the application and subsequent removal of negative pressure to the removed fluid canister circuit 202 of steps 806 and 808.

As noted above, the method 800 of FIGS. 8A-8E may be performed in substantially the same manner as the method 600 described with references to FIG. 6A above. However, whereas, as described above with reference to the method of FIGS. 6A-6E, according to various embodiments, any range of negative pressures may generally be applied to the negative pressure circuit 200 at step 604 of method 600, the negative pressure applied to the negative pressure circuit 200 at step 802 of the method 800 must be limited to negative pressures that will not result in the fluid 121 at the wound site 114 being displaced into the removed fluid canister 106.

Following the completion of step 808, the controller 118 may be configured to calculate the volume of the dead space 119a at the wound site 114 (which corresponds to the maximum volume of additional instillation fluid 105 that may be delivered to wound site 114) at step 508 of method 500 of FIG. 5. More specifically at step 508, after calculating the volumes of the removed fluid canister circuit 202 and the negative pressure circuit 200 based on the parameters measured at steps 804 and 808 (in a manner similar to that described with reference to step 612 of the method 600 of FIGS. 6A-6G), the dead space 119a at the wound site 114 may be calculated based on subtracting the measured volume of the removed fluid canister circuit 202 from the measured volume of the negative pressure circuit 200, with the volume of the removed fluid canister circuit 202 of the method 800 of FIGS. 8A-8E being defined by the dead space 103a of the removed fluid canister 106, conduit 136 and upstream tubing portion 110a; and the volume of the negative pressure circuit 200 being defined by the volume of the removed fluid canister circuit 202 (i.e. dead space 103a of the removed fluid canister 106, conduit 136 and upstream tubing portion 110a), the downstream tubing portion 110b, dead space 119a of the wound site 114 and the portion of downstream instillation tubing 108b extending between the drape layer 117 and instillation tubing valve 109.

According to various embodiments, in embodiments of method 500 in which the determination of the volume of the dead space 119a at the wound site 114 at step 508 is based on measured parameters related to the removed fluid canister circuit 202 and negative pressure circuit 200 obtained using the method 800 of FIGS. 8A-8E, step 508 may also include subtracting or otherwise adjusting the calculated difference between the volumes of the removed fluid canister circuit 202 and the negative pressure circuit 200 to account for/ factor in the known volumes of the downstream tubing portion 110b and the portion of the downstream instillation tubing 108b extending between the drape layer 117 and the instillation tubing valve 109 into the determination of the volume of the dead space 119a at the wound site 114.

Although, as described above, in some embodiments of method 500, additional instillation fluid 105 may be delivered at step 516 without first removing any remaining fluid 121 at the wound site 114, according to other embodiments, it may be desirable to remove fluid 121 from the wound site 114 prior to the delivery of additional instillation fluid 105.

Referring to FIGS. 9A-9E, one embodiment of a method 900 of determining an amount of dead space at a wound site 114 which may be used at step 506 of the method 500 of FIG. 5 in embodiments in which it is desired to remove fluid 121 from the wound site 114 prior to instilling additional instillation fluid 105 is illustrated. In particular, according to the method 900 of FIGS. 9A-9E, any fluid 121 initially at the wound site 114 immediately prior to step 506 (e.g. as shown in FIG. 7) is displaced from the wound site 114 during the method 900 (i.e. step 506), such the final dead space 119b into which the additional instillation fluid 121 will be instilled will be greater than the initial dead space 119a at the wound site that is present immediately prior to the initiation of step 506 by an amount generally corresponding to a volume of the fluid 121 displaced from the wound site 114 to the removed fluid canister 106 during the method 900.

As shown by the flowchart in FIG. 9A, the method 900 of determining dead space is substantially the same as the method 600 of calculating the dead space 119 upon initial instillation of instillation fluid 105 to the wound site 114 at step 502 (discussed in more detail with reference to FIGS. 6A-6G). In particular, similar to steps 604 and 606, the method 900 of FIG. 9A also includes steps 902 and 904 (shown, e.g. in FIGS. 9B and 9C, respectively) during which negative pressure is applied to and removed from the negative pressure circuit 200. Similar to steps 608 and 610 of the method 600 of FIG. 6A, the method 900 of FIG. 9 also includes steps 906 and 908 (shown, e.g. in FIGS. 9D and 9E, respectively) during which negative pressure is applied to and removed from the removed fluid canister circuit 202.

Figure 9A:
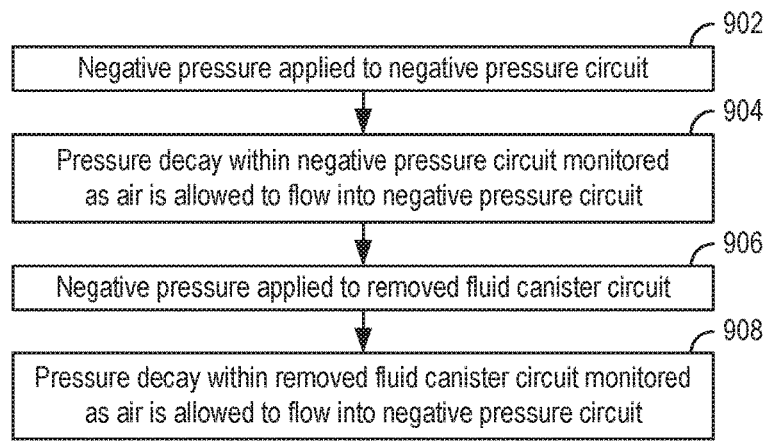
FIG. 9A is a flowchart of method of instilling an additional quantity of fluid to a wound site to the negative pressure wound therapy system of FIG. 7, according to an exemplary embodiment.
Figure 9B:
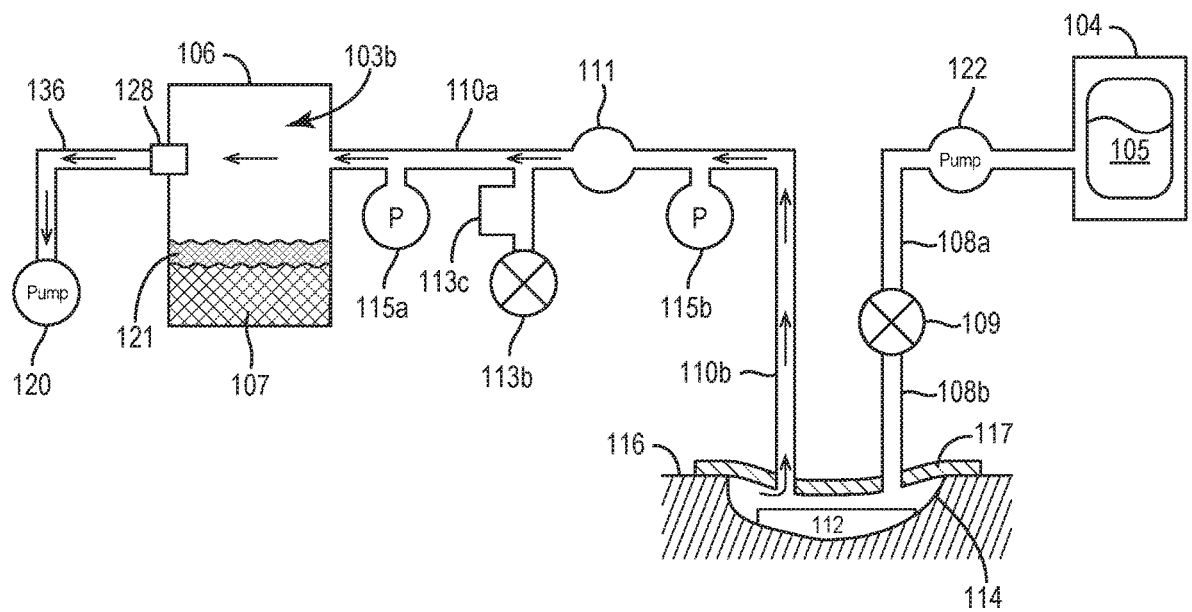
FIG. 9B illustrates the negative pressure wound therapy system of FIG. 7 following an application of a first negative pressure to the negative pressure wound therapy system, according to an exemplary embodiment.
Figure 9C:
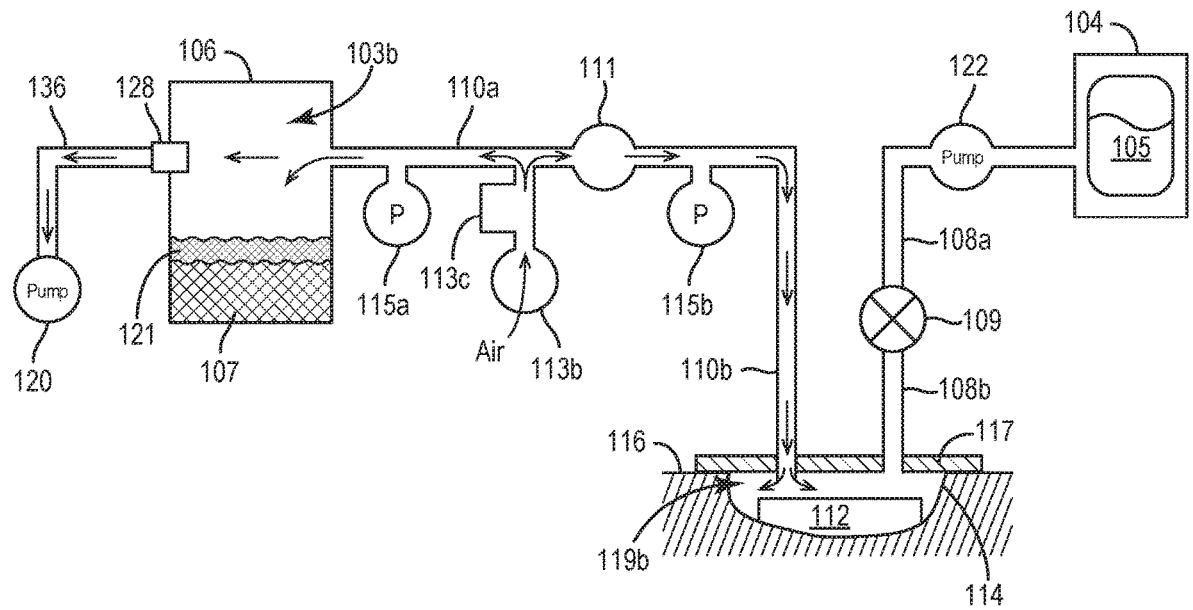
FIG. 9C illustrates the negative pressure wound therapy system of FIG. 9B during venting of the negative pressure wound therapy system following the application of the first negative pressure as shown in FIG. 9B, according to an exemplary embodiment.
Figure 9D:
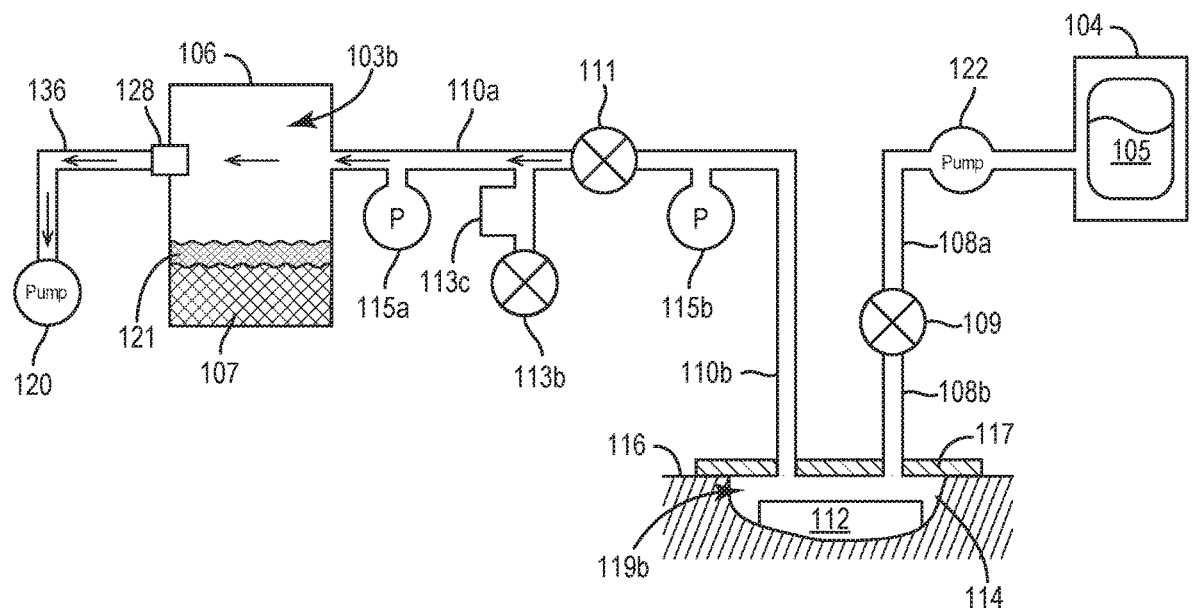
FIG. 9D illustrates the negative pressure wound therapy system of FIG. 7 following an application of a second negative pressure to the negative pressure wound therapy system, according to an exemplary embodiment.
Figure 9E:
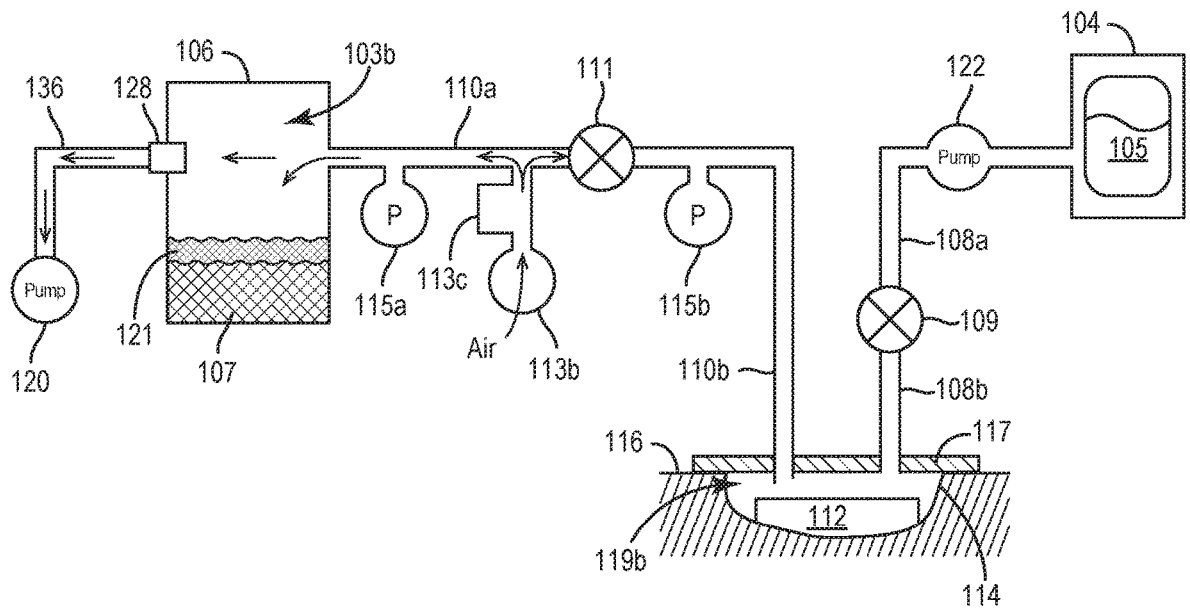
FIG. 9E illustrates the negative pressure wound therapy system of FIG. 9D during venting of the negative pressure wound therapy system following the application of the first negative pressure as shown in FIG. 9D, according to an exemplary embodiment.

However, unlike the method 600 of FIG. 6A in which the application and subsequent removal of negative pressure to the negative pressure circuit 200 at steps 604 and 608 may be performed either prior to or after the application and subsequent removal of negative pressure to the removed fluid canister circuit 202 of steps 610 and 612, in the method 900 of FIG. 9A, the application and subsequent removal of negative pressure to the negative pressure circuit 200 at steps 902 and 904 is performed prior to the application and subsequent removal of negative pressure to the removed fluid canister circuit 202 of steps 906 and 908. Additionally, whereas, as described above with reference to the method of FIGS. 6A-6E, according to various embodiments, any range of negative pressures may generally be applied to the negative pressure circuit 200 at step 604 of method 600, the negative pressure applied to the negative pressure circuit 200 at step 902 of the method 900 of FIG. 9A must be sufficient to cause the displacement of fluid 121 from the wound site 114 into the removed fluid canister 106.

Following the completion of step 908, the controller 118 may be configured to calculate the volume of the final dead space 119b at the wound site 114 (which corresponds to the maximum volume of additional instillation fluid 105 that may be delivered to wound site 114) at step 508 of method 500 of FIG. 5. More specifically at step 508, after calculating the volumes of the removed fluid canister circuit 202 and the negative pressure circuit 200 based on the parameters measured at steps 904 and 908 (in a manner similar to that described with reference to step 612 of the method 600 of FIGS. 6A-6G), the final dead space 119b at the wound site 114 may be calculated based on subtracting the measured volume of the removed fluid canister circuit 202 from the measured volume of the negative pressure circuit 200, with the volume of the removed fluid canister circuit 202 of the method 800 of FIGS. 9A-9E being defined by the final dead space 103b of the removed fluid canister 106 (with the final dead space 103b of the removed fluid canister 106 being generally equal to the difference between an initial dead space 103a within the removed fluid canister 106 and the volume of fluid 121 displaced into the removed fluid canister 106 from the wound site 114 at step 802, as shown, e.g. in FIG. 9B), conduit 136 and upstream tubing portion 110a; and the volume of the negative pressure circuit 200 being defined by the volume of the removed fluid canister circuit 202 (i.e. final dead space 103b of the removed fluid canister 106, conduit 136 and upstream tubing portion 110a), the downstream tubing portion 110b, final dead space 119b of the wound site 114 and the portion of downstream instillation tubing 108b extending between the drape layer 117 and instillation tubing valve 109.

According to various embodiments, in embodiments of method 500 in which the determination of the volume of the dead space 119 at the wound site 114 at step 508 is based on measured parameters related to the removed fluid canister circuit 202 and negative pressure circuit 200 obtained using the method 900 of FIGS. 9A-9E, step 508 may also include subtracting or otherwise adjusting the calculated difference between the volumes of the removed fluid canister circuit 202 and the negative pressure circuit 200 to account for/factor in the known volumes of the downstream tubing portion 110b and the portion of the downstream instillation tubing 108b extending between the drape layer 117 and the instillation tubing valve 109 into the determination of the volume of the dead space 119a at the wound site 114.

In some embodiments of method 500 of FIG. 5 in which fluid 121 from the wound site 114 is removed prior to the instillation of additional instillation fluid 105 at step 516, it may be desirable to ensure that the initial dead space 103a in the removed fluid canister 106 immediately prior to beginning the step of determining dead space at the wound site at step 506 is sufficient to hold fluid 121 that will be displaced from the wound site 114 into the removed fluid canister during step 506, so as to avoid the risk of removed fluid canister 106 overflow.

Accordingly, in some embodiments of method 500 in which fluid 121 from the wound site 114 is removed prior to the instillation of any additional instillation fluid 105 at step 516, the method of step 506 of determining dead space at the wound site 114 (e.g., such as described with reference to the method 900 of FIGS. 9A-9E) may include determining whether there is sufficient dead space at the removed fluid canister 106 to hold the fluid 121 from the wound site 114 that may be displaced into the removed fluid canister 106 as part of the method of determining dead space at the wound site 114.

Figure 10A:
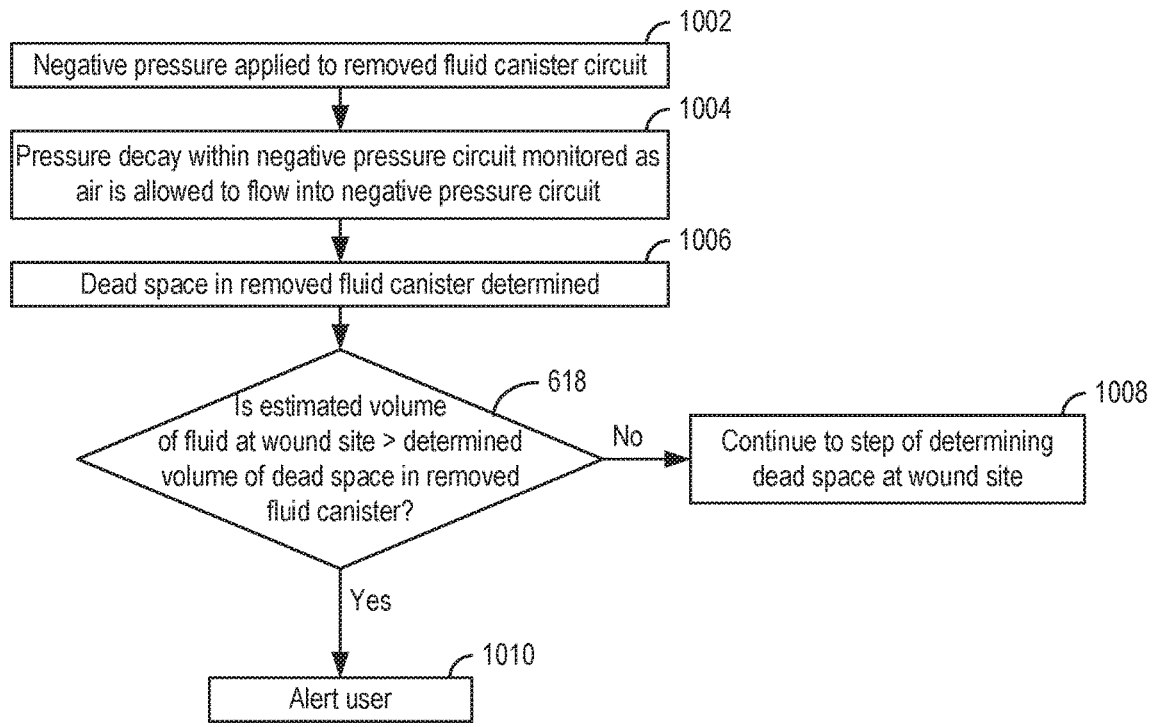
FIG. 10A is a flowchart of a method of determining whether sufficient dead space is present in a negative pressure wound therapy system, according to an exemplary embodiment.
Figure 10B:
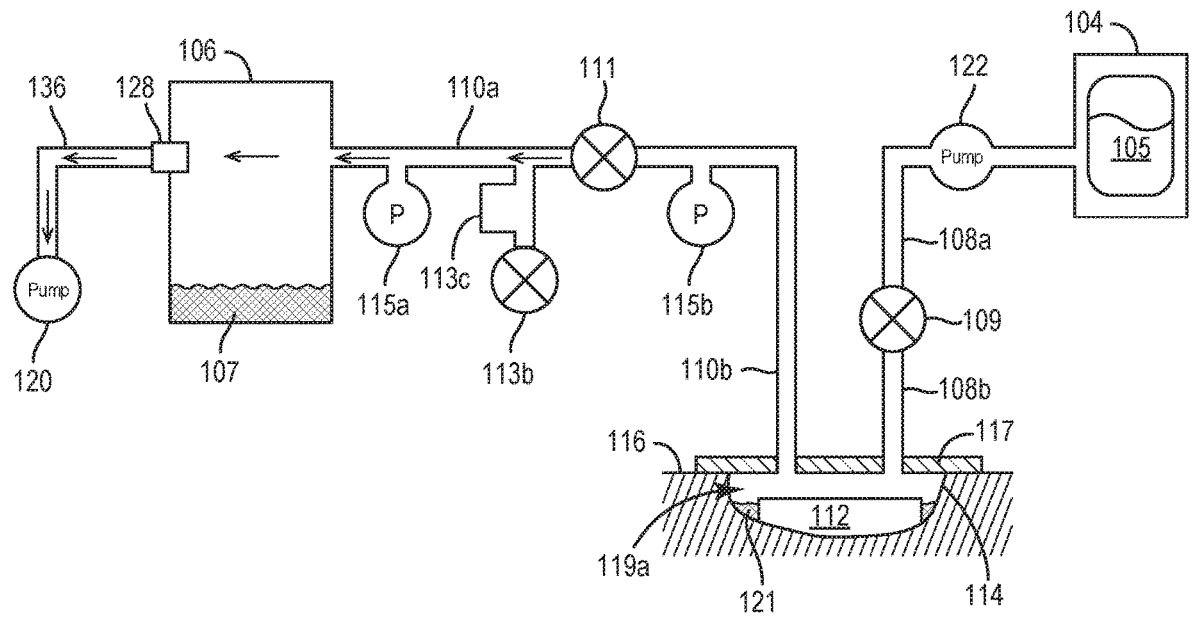
FIG. 10B illustrates the negative pressure wound therapy system of FIG. 7 following an application of a first negative pressure to the negative pressure wound therapy system, according to an exemplary embodiment.
Figure 10C:
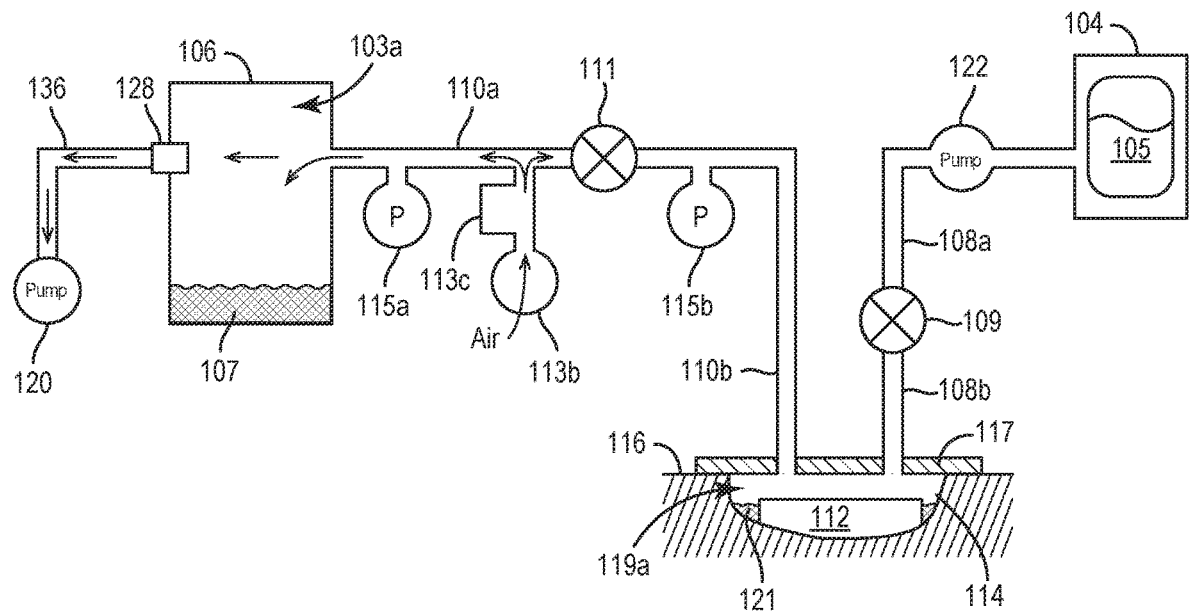
FIG. 10C illustrates the negative pressure wound therapy system of FIG. 10B during venting of the negative pressure wound therapy system following the application of the first negative pressure as shown in FIG. 10B, according to an exemplary embodiment.

Illustrated in FIGS. 10A-10C is one embodiment of such a method that may be used to minimize the risk of overflow of the removed fluid canister 106 during step 506 in which dead space at the wound site 114 is being determined (e.g., via method 900 as described in FIGS. 9A-9E). At steps 1002 and 1004 (shown in FIGS. 10B and 10C, respectively) negative pressure is applied to and removed from the removed fluid canister circuit 202 to determine the initial dead space 103a in the removed fluid canister 106 prior to beginning step 506 (e.g. as shown in FIG. 7). In general, the steps 1002 and 1004 of the method 1000 of FIGS. 10A-10E may be performed in a manner substantially similar to the manner in which steps 608 and 610 of the method 600 of FIGS. 6A-6G are performed. At step 1006, the volume of the removed fluid canister circuit 202 is calculated based on the parameter measured at step 1004 (in a manner similar to that described with reference to step 612 of the method 600 of FIGS. 6A-6G). Once the volume of the removed fluid canister circuit 202 has been calculated, the known volumes of the conduit 136 and the upstream tubing portion 110a may be subtracted from the calculated removed fluid canister circuit 202 to determining the volume of the initial dead space 103a in the removed fluid canister 106 (i.e. the maximum volume of fluid 121 displaced from the wound site 114 that the removed fluid canister 106 may hold).

Once the volume of the initial dead space 103a has been calculated at step 1006, at step 1008, the controller 118 may be configured to estimate the volume of the fluid 121 at the wound site 114 at the time immediately preceding the determination of dead space at the wound site 114 at step 506. The volume of the fluid 121 at the wound site 114 may be based on any number of different factors and variables such as, e.g. stored values of quantities of instillation fluid 105 previously delivered to the wound site 114, stored values of fluid 121 previously removed from the wound site, elapsed time (e.g. from a prior instillation, a prior removal of fluid 121, etc.), etc., with the controller 118 at step 1008 further being configured to compare this estimated volume of fluid 121 to the initial dead space 103a calculated at step 1006, alerting the user to empty the removed fluid canister 106 at step 1010 if the controller 118 determines that the estimated fluid 121 volume exceeds the calculated initial dead space 103a. If the calculated initial dead space 103a is sufficient to hold the estimated volume fluid 121 from the wound site 114, at step 1012 the controller 1012 may be configured to begin the step 506 of determining dead space at the wound site 114, e.g. according to method 900 as described with reference to FIGS. 9A-9E.

As noted above, according to some embodiments of method 500, it may be advantageous to monitor changes in the volume of the wound site 114 to track the progress of the healing of the wound site 114 at an optional step 510.

In general, the volume of the wound site 114 is defined by the entirety of the interior extending between the wound site 114 and the drape layer 117 attached to the skin 116 about the wound site 114. At various points during treatment using the NPWT system 100, located within and defining the volume of the wound site may be any one of, and any combination of: the wound dressing 112, fluid 121, and/or dead space 119. As will be understood, unless the wound dressing 112 is replaced during treatment, the volume of the wound site 114 volume occupied by the wound dressing 112 will generally remain unchanged over the course of treatment, whereas the portion of the wound site 114 volume occupied by the fluid 121 and/or dead space 119 may change with time.

Figure 11:
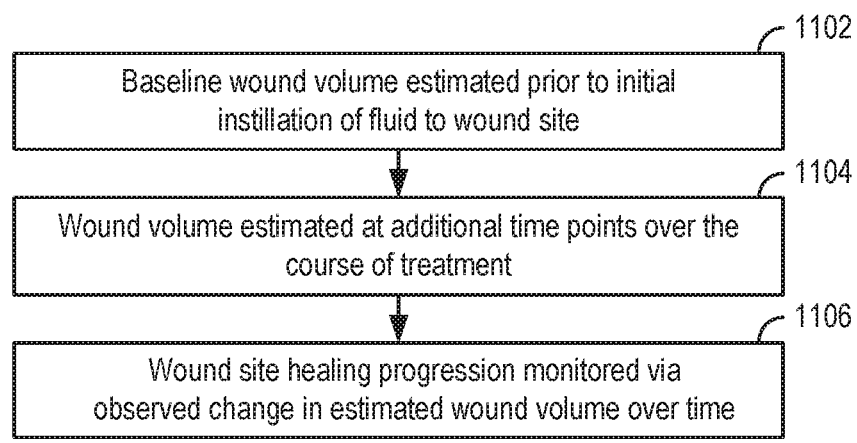
FIG. 11 is a flowchart of a process for monitoring the healing progression of the wound site over time, according to an exemplary embodiment.

Referring to FIG. 11, a block diagram illustrating one embodiment of a method 1100 of tracking wound site 114 healing progression which may be used at step 510 of the method 500 of FIG. 5 is illustrated. At step 1102, an initial volume of the wound site 114 is estimated and recorded by the controller 118 at a point in time prior to an initial instillation of instillation fluid 105 to the wound site 114, and may serve as a baseline against which subsequent wound site 114 volume estimates are compared to to track healing progress. According to various embodiments, estimation of the initial volume of the wound site 114 at step 1102 may be performed according to (or as) step 616 of method 600 described with reference to FIGS. 6A-6G.

At step 1104, the estimated volume of the wound site 114 is determined and recorded at one or more additional times during treatment (e.g., once per day) following the estimation of the initial wound site 114 volume at step 1102, with the times at which such one or more wound site 114 volumes are estimated and the values of the determined wound site 114 volume being stored as data points within the memory of therapy device 102 and/or presented to a user as an output of therapy device 102 (e.g., via communications interface 124 or user interface 126). In some embodiments, the estimated wound volume can be plotted as a function of time.

The additional wound site 114 volume estimates determined at one or more additional times over the course of treatment at step 1104 may be estimated according to any number of different processes. For example, according to some embodiments, the wound site 114 volume estimates recorded at step 1104 may be based on the final dead space volume at the wound site 114 calculated, e.g., at step 508 of method 500 and/or using method 900 as described with reference to FIG. 5 and or 9A-9E, respectively.

As shown at step 510 of FIG. 5 and step 616 of FIG. 6A, according to some embodiments, the wound site 114 volume estimates at steps 1102 and/or steps 1104 may be performed in conjunction with method of delivering of instillation fluid 105 to the wound site 114. However, as will be understood, according to other embodiments the determination of and recording of some, all, or none of the wound site 114 volume estimates at steps 1102 and/or steps 1104 may be performed independent of any delivery of instillation of instillation fluid 105 to the wound site 114.

As additional wound site 114 volume estimates are obtained at steps 1104, at step 1106, changes in the estimated wound site 114 volumes over time may be used to determine healing progression of the wound site 114. For example, step 1106 may include comparing wound site 114 volume estimates obtained at step 1104 to one or more previous estimates of the wound site 114 volume (obtained at either step 1104 or step 1102) to identify a change in the wound site 114 volume. In some embodiments, step 1006 may additionally include determining a rate at which the wound site 114 is healing based on the changes in the estimated wound site 114 volume over time. In some embodiments, step 1106 may include extrapolating or predicting a time at which wound site 114 will be fully healed based on the series of wound site 114 volume estimates stored by the controller 118. For example, step 1106 may include predicting a time at which the estimated wound site 114 volume will reach zero (or another threshold value) based on the initial wound site 114 volume estimate obtained at step 1002 and the series of additional wound site 114 volume estimates obtained at step 1004.

As will be understood, according to various embodiments, the controller 118 may be programmed to allow the NPWT system 100 to determine volume relative to the wound site 114 using any or all of the methods described herein. Accordingly, while in some embodiments the controller 118 may optionally be preprogrammed to automatically determine a volume of instillation fluid 105 to be delivered according to a particular method (e.g. the method 900 embodiment illustrated in FIGS. 9A-9E), the controller 118 may optionally also allow a user to select any of the other modes of calculating a volume relative to the wound site 114 based on whether the user desires to, e.g.: remove fluid 121 from the wound site 114 prior to instillation of additional instillation fluid 105; verify sufficient dead space 103a in the removed fluid canister 106 prior to determining the dead space at the wound site 114; verify sufficient dead space 103b in the removed fluid canister 106 prior to the instillation of a calculated quantity of additional instillation fluid 105 to be delivered to the wound site 114; monitor changes in the wound site 114 volume to track healing progression; etc.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

We claim:

1. A wound therapy system comprising:
a therapy device comprising:
a canister configured to collect wound exudate from a wound; and
a pump fluidly coupled to the canister and configured to draw a negative pressure within the canister;
tubing having a first end and a second end, the first end being attached to and fluidly coupled to the canister;
a valve coupled to the tubing at a position located between the first end and the second end of the tubing, the valve configured to prevent flow if a threshold minimum negative pressure is not met and to permit flow if the threshold negative pressure is met;
a first tubing portion defined between the first end of the tubing and the valve and a second tubing portion defined between the second end of the tubing and the valve; and
an opening formed through the first tubing portion, the opening configured to allow for fluid communication between the first tubing portion and an ambient pressure atmosphere, and the second end of the tubing is attached to a wound dressing configured to be sealed to a surface to define a treatment space, the fluid canister being in fluid communication with the treatment space when the valve is subject to a pressure that is less than or equal to the threshold minimum negative pressure;
a controller configured to:
operate the pump to draw a predetermined first negative pressure in the canister, the first predetermined negative pressure being greater than the threshold minimum negative pressure;
calculate a first volume based on a measured time required for pressure within the canister to increase from the predetermined first negative pressure to a predetermined baseline pressure;
operate the pump to draw a predetermined second negative pressure within the canister and the treatment space, the second predetermined negative pressure being less than the threshold minimum negative pressure;
calculate a second volume based on a measured time required for pressure within the canister and the treatment space to increase from the predetermined second negative pressure to the predetermined baseline pressure; and
calculate the volume of the treatment space based on the difference between the first calculated volume and the second calculated volume.

2. The wound therapy system of claim 1, wherein the tubing is defined by an outer wall, the opening extending through the outer wall of the tubing.

3. The wound therapy system of claim 1, the controller further being configured to calculate a volume of the treatment space based on subtracting a known volume of the tubing from a calculated difference between the first calculated volume and the second calculated volume.

4. The wound therapy system of claim 1, further comprising a calibrated leak detector fluidly connected to the opening of the tubing, the leak detector being configured to measure the rate of air flow through the opening.

5. The wound therapy system of claim 4, wherein the calculations of the first volume and the second volume by the controller are each based on the rate of air flow through the opening detected by the leak detector.

6. The wound therapy system of claim 1, the valve being configured to remain in an open configuration in which the first tubing portion and the second tubing portion are in fluid communication following the valve being subject to the threshold minimum negative pressure.

7. The wound therapy system of claim 6, the valve being resettable from the open configuration to the initial closed valve configuration in which fluid communication between the first tubing portion and the second tubing portion is prevented by the valve until a pressure less than or equal to the threshold negative pressure is met.

8. The wound therapy system of claim 1, further comprising a first pressure sensor in fluid communication with the first tubing portion.

9. A wound therapy system comprising:
   a therapy device comprising:
      a canister configured to collect wound exudate from a wound; and
      a pump fluidly coupled to the canister and configured to draw a negative pressure within the canister;
   tubing having a first end and a second end, the first end being attached to and fluidly coupled to the canister;
   a valve coupled to the tubing at a position located between the first end and the second end of the tubing, the valve configured to prevent flow if a threshold minimum negative pressure is not met and to permit flow if the threshold negative pressure is met;
   a first tubing portion defined between the first end of the tubing and the valve and a second tubing portion defined between the second end of the tubing and the valve;
   a first pressure sensor in fluid communication with the first tubing section;
   a controller configured to:
      operate the pump to draw a predetermined first negative pressure in the canister, the first predetermined negative pressure being greater than the threshold minimum negative pressure;
      calculate a first volume based on a measured time required for pressure within the canister to increase from the predetermined first negative pressure to a predetermined baseline pressure; and
      stop operation of the pump following a predetermined time interval after detection of the predetermined first negative pressure within the first tubing portion by the first pressure sensor.

10. The wound therapy system of claim 9, further comprising a second pressure sensor in fluid communication with the second tubing portion.

11. The wound therapy system of claim 10, wherein, the controller is further configured to:
   operate the pump to draw a predetermined second negative pressure within the canister and the treatment space, the second predetermined negative pressure being less than the threshold minimum negative pressure,
   calculate a second volume based on a measured time required for pressure within the canister and the treatment space to increase from the predetermined second negative pressure to the predetermined baseline pressure; and
   stop operation of the pump following a predetermined time interval after detection of the predetermined second negative pressure within the second tubing portion by the second pressure sensor.

12. The wound therapy system of claim 11, further comprising an opening formed through the first tubing portion, the opening configured to allow for fluid communication between the first tubing portion and an ambient pressure atmosphere, and wherein the opening in the tubing defines a calibrated leak having a known dimension through which air from the ambient pressure atmosphere may flow into the tubing.

* * * * *